(12) United States Patent
Frieden et al.

(10) Patent No.: US 12,386,895 B2
(45) Date of Patent: Aug. 12, 2025

(54) SYSTEMS AND METHODS FOR GENETIC ANALYSIS

(71) Applicant: Laboratory Corporation of America Holdings, Burlington, NC (US)

(72) Inventors: Alexander Frieden, Somerville, MA (US); Caleb J. Kennedy, Arlington, MA (US); Xavier S. Haurie, Belmont, MA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 1359 days.

(21) Appl. No.: 17/000,054

(22) Filed: Aug. 21, 2020

(65) Prior Publication Data

US 2021/0089581 A1 Mar. 25, 2021

Related U.S. Application Data

(63) Continuation of application No. 14/826,595, filed on Aug. 14, 2015, now abandoned.

(60) Provisional application No. 62/037,861, filed on Aug. 15, 2014.

(51) Int. Cl.
| | |
|---|---|
| *G06F 16/901* | (2019.01) |
| *G06F 16/9038* | (2019.01) |
| *G16B 20/00* | (2019.01) |
| *G16B 20/20* | (2019.01) |
| *G16B 20/40* | (2019.01) |
| *G16B 50/00* | (2019.01) |
| *G16B 50/30* | (2019.01) |

(52) U.S. Cl.
CPC ...... *G06F 16/9024* (2019.01); *G06F 16/9038* (2019.01); *G16B 20/20* (2019.02); *G16B 20/40* (2019.02); *G16B 50/00* (2019.02); *G16B 50/30* (2019.02); *G16B 20/00* (2019.02)

(58) Field of Classification Search
None
See application file for complete search history.

(56) References Cited

U.S. PATENT DOCUMENTS

| | | |
|---|---|---|
| 3,781,120 A | 12/1973 | Engelhardt |
| 4,149,852 A | 4/1979 | Tiru et al. |
| 4,683,195 A | 7/1987 | Mullis et al. |
| 4,683,202 A | 7/1987 | Mullis |
| 4,988,617 A | 1/1991 | Landegren et al. |
| 5,060,980 A | 10/1991 | Johnson et al. |
| 5,210,015 A | 5/1993 | Gelfand et al. |
| 5,225,165 A | 7/1993 | Perlman |
| 5,234,809 A | 8/1993 | Boom et al. |
| 5,242,794 A | 9/1993 | Whiteley et al. |
| 5,253,551 A | 10/1993 | DeVaughn |
| 5,342,328 A | 8/1994 | Grossman et al. |
| 5,348,853 A | 9/1994 | Wang et al. |
| 5,382,408 A | 1/1995 | Perlman |
| 5,456,887 A | 10/1995 | Calvo et al. |
| 5,459,307 A | 10/1995 | Klotz |
| 5,486,686 A | 1/1996 | Zdybel et al. |
| 5,494,810 A | 2/1996 | Barany et al. |
| 5,567,583 A | 10/1996 | Wang et al. |
| 5,583,024 A | 12/1996 | McElroy et al. |
| 5,604,097 A | 2/1997 | Brenner |
| 5,636,400 A | 6/1997 | Young |
| 5,674,713 A | 10/1997 | McElroy et al. |
| 5,695,934 A | 12/1997 | Brenner |
| 5,700,673 A | 12/1997 | McElroy et al. |
| 5,701,256 A | 12/1997 | Marr et al. |
| 5,720,406 A | 2/1998 | Fassbind et al. |
| 5,830,064 A | 11/1998 | Bradish et al. |
| 5,846,719 A | 12/1998 | Brenner et al. |
| 5,863,722 A | 1/1999 | Brenner |
| 5,866,337 A | 2/1999 | Schon |

(Continued)

FOREIGN PATENT DOCUMENTS

| | | |
|---|---|---|
| EP | 1321477 A1 | 6/2003 |
| EP | 1564306 A2 | 8/2005 |

(Continued)

OTHER PUBLICATIONS

Mey, 2010, Rapid, low-input, low-bias construction of shotgun fragment libraries by high-density in vitro transposition, Genome Biol 11 :R 119.
Agrawal, 1990, Site-specific functionalization of oligodeoxynucleotides for non-radioactive labelling, Tetrahedron Let 31 :1543-1546.
Alkan, 2009, Personalized copy number and segmental duplication maps using next-generation seqeuncing, Nature Genetics 41(10):1061-1068.
Archer, 2014, Selective and flexible depletion of problematic sequences from RNA-seq libraries at the cDNA stage, BMC Genomics 15(1):401.
Balzer, 2013, Filtering duplicate reads from 454 pyrosequencing data, Bioinformatics 29(7):830-836.

(Continued)

*Primary Examiner* — Olivia M. Wise
*Assistant Examiner* — Jonathan Edward Hayes
(74) *Attorney, Agent, or Firm* — Wolf, Greenfield & Sacks, P.C.

(57) ABSTRACT

The invention relates to using a graph database in genetic analyses to link mutation data to extrinsic data. Entities such as mutations, patients, samples, alleles, and clinical information are individually represented and stored as nodes and relationships between entities are also individually represented and stored. Each node and relationship can be stored using a fixed-size record and nodes can be flexibly invoked to represent any entity without disrupting the existing data. Systems and methods of the invention may be used for obtaining data representing a mutation in an individual and using a node in a graph database to store a description of the mutation. The node has stored within it a pointer to an adjacent node that provides information about a clinical significance of the variant. The graph database can be queried to provide a report of the clinical significance of the mutation.

17 Claims, 14 Drawing Sheets

(56) References Cited

U.S. PATENT DOCUMENTS

| | | |
|---|---|---|
| 5,869,252 A | 2/1999 | Bouma et al. |
| 5,869,717 A | 2/1999 | Frame et al. |
| 5,871,921 A | 2/1999 | Landegren et al. |
| 5,888,788 A | 3/1999 | De Miniac |
| 5,971,921 A | 8/1999 | Zhang et al. |
| 5,993,611 A | 11/1999 | Moronet et al. |
| 5,994,056 A | 11/1999 | Higuchi |
| 6,033,854 A | 3/2000 | Kurnit et al. |
| 6,033,872 A | 3/2000 | Bergsma et al. |
| 6,100,099 A | 8/2000 | Gordon et al. |
| 6,138,077 A | 10/2000 | Brenner |
| 6,150,516 A | 11/2000 | Brenner et al. |
| 6,171,785 B1 | 1/2001 | Higuchi |
| 6,172,214 B1 | 1/2001 | Brenner |
| 6,172,218 B1 | 1/2001 | Brenner |
| 6,179,819 B1 | 1/2001 | Haswell |
| 6,197,508 B1 | 3/2001 | Stanley |
| 6,197,574 B1 | 3/2001 | Miyamoto et al. |
| 6,210,891 B1 | 4/2001 | Nyren et al. |
| 6,223,128 B1 | 4/2001 | Allex et al. |
| 6,235,472 B1 | 5/2001 | Landegren et al. |
| 6,235,475 B1 | 5/2001 | Brenner et al. |
| 6,235,501 B1 | 5/2001 | Gautsch et al. |
| 6,235,502 B1 | 5/2001 | Weissman et al. |
| 6,258,568 B1 | 7/2001 | Nyren |
| 6,274,320 B1 | 8/2001 | Rothberg et al. |
| 6,306,597 B1 | 10/2001 | Macevicz |
| 6,335,200 B1 | 1/2002 | Tiru et al. |
| 6,352,828 B1 | 3/2002 | Brenner |
| 6,360,235 B1 | 3/2002 | Tilt et al. |
| 6,361,940 B1 | 3/2002 | Van Ness et al. |
| 6,403,320 B1 | 6/2002 | Read et al. |
| 6,462,254 B1 | 10/2002 | Vernachio et al. |
| 6,489,105 B1 | 12/2002 | Matlashewski et al. |
| 6,558,928 B1 | 5/2003 | Landegren |
| 6,569,920 B1 | 5/2003 | Wen et al. |
| 6,582,938 B1 | 6/2003 | Su et al. |
| 6,585,938 B1 | 7/2003 | Machida et al. |
| 6,613,516 B1 | 9/2003 | Christians et al. |
| 6,714,874 B1 | 3/2004 | Myers et al. |
| 6,716,580 B2 | 4/2004 | Gold et al. |
| 6,719,449 B1 | 4/2004 | Laugham et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,858,412 B2 | 2/2005 | Willis et al. |
| 6,911,345 B2 | 6/2005 | Quake et al. |
| 6,913,879 B1 | 7/2005 | Schena |
| 6,927,024 B2 | 8/2005 | Dodge et al. |
| 6,941,317 B1 | 9/2005 | Chamberlin et al. |
| 6,948,843 B2 | 9/2005 | Laugham et al. |
| 7,034,143 B1 | 4/2006 | Preparata et al. |
| 7,041,481 B2 | 5/2006 | Anderson et al. |
| 7,049,077 B2 | 5/2006 | Yang |
| 7,057,026 B2 | 6/2006 | Barnes et al. |
| 7,071,324 B2 | 7/2006 | Preparata et al. |
| 7,074,564 B2 | 7/2006 | Landegren |
| 7,074,586 B1 | 7/2006 | Cheronis et al. |
| 7,115,400 B1 | 10/2006 | Adessi et al. |
| 7,169,560 B2 | 1/2007 | Rothberg et al. |
| 7,232,656 B2 | 6/2007 | Balasubramanian et al. |
| 7,244,559 B2 | 7/2007 | Rothberg et al. |
| RE39,793 E | 8/2007 | Brenner |
| 7,253,117 B2 | 8/2007 | Donohoe et al. |
| 7,282,337 B1 | 10/2007 | Harris |
| 7,297,518 B2 | 11/2007 | Quake et al. |
| 7,320,860 B2 | 1/2008 | Landegren et al. |
| 7,323,305 B2 | 1/2008 | Leamon et al. |
| 7,335,762 B2 | 2/2008 | Rothberg et al. |
| 7,351,528 B2 | 4/2008 | Landegren |
| 7,393,665 B2 | 7/2008 | Brenner |
| 7,510,829 B2 | 3/2009 | Faham et al. |
| 7,537,889 B2 | 5/2009 | Sinha et al. |
| 7,537,897 B2 | 5/2009 | Brenner et al. |
| 7,544,473 B2 | 6/2009 | Brenner |
| 7,582,431 B2 | 9/2009 | Drmanac et al. |
| 7,598,035 B2 | 10/2009 | Macevicz |
| 7,629,151 B2 | 12/2009 | Gold et al. |
| 7,642,056 B2 | 1/2010 | Ahn et al. |
| 7,666,593 B2 | 2/2010 | Lapidus |
| 7,700,323 B2 | 4/2010 | Willis et al. |
| 7,774,962 B1 | 8/2010 | Ladd |
| 7,776,616 B2 | 8/2010 | Heath et al. |
| RE41,780 E | 9/2010 | Anderson et al. |
| 7,790,388 B2 | 9/2010 | Landegren et al. |
| 7,809,509 B2 | 10/2010 | Milosavljevic |
| 7,835,871 B2 | 11/2010 | Kain et al. |
| 7,862,999 B2 | 1/2011 | Zheng et al. |
| 7,865,534 B2 | 1/2011 | Genstruct |
| 7,883,849 B1 | 2/2011 | Dahl |
| 7,957,913 B2 | 6/2011 | Chinitz et al. |
| 7,960,120 B2 | 6/2011 | Rigatti et al. |
| 7,985,716 B2 | 7/2011 | Yershov et al. |
| 7,993,880 B2 | 8/2011 | Willis et al. |
| 8,024,128 B2 | 9/2011 | Rabinowitz et al. |
| 8,114,027 B2 | 2/2012 | Triva |
| 8,165,821 B2 | 4/2012 | Zhang |
| 8,195,415 B2 | 6/2012 | Fan et al. |
| 8,209,130 B1 | 6/2012 | Kennedy et al. |
| 8,283,116 B1 | 10/2012 | Bhattacharyya et al. |
| 8,462,161 B1 | 6/2013 | Barber |
| 8,463,895 B2 | 6/2013 | Arora et al. |
| 8,474,228 B2 | 7/2013 | Adair et al. |
| 8,496,166 B2 | 7/2013 | Burns et al. |
| 8,529,744 B2 | 9/2013 | Marziali et al. |
| 8,778,609 B1 | 7/2014 | Umbarger |
| 8,812,422 B2 | 8/2014 | Nizzari et al. |
| 8,847,799 B1 | 9/2014 | Kennedy et al. |
| 8,976,049 B2 | 3/2015 | Kennedy et al. |
| 9,074,244 B2 | 7/2015 | Sparks et al. |
| 9,115,387 B2 | 8/2015 | Umbarger |
| 9,228,233 B2 | 1/2016 | Kennedy et al. |
| 9,292,527 B2 | 3/2016 | Kennedy et al. |
| D773,070 S | 11/2016 | Porreca et al. |
| 9,535,920 B2 | 1/2017 | Kennedy et al. |
| 9,567,639 B2 | 2/2017 | Oliphant et al. |
| 9,677,124 B2 | 6/2017 | Umbarger |
| 10,061,953 B2 | 8/2018 | Porreca et al. |
| 10,227,635 B2 | 3/2019 | Umbarger et al. |
| 2001/0007742 A1 | 7/2001 | Landergren |
| 2001/0046673 A1 | 11/2001 | French et al. |
| 2002/0001800 A1 | 1/2002 | Lapidus |
| 2002/0040216 A1 | 4/2002 | Dumont et al. |
| 2002/0091666 A1 | 7/2002 | Rice et al. |
| 2002/0129525 A1 | 9/2002 | Kissinger et al. |
| 2002/0182609 A1 | 12/2002 | Arcot |
| 2002/0187496 A1 | 12/2002 | Andersson et al. |
| 2002/0190663 A1 | 12/2002 | Rasmussen |
| 2003/0166057 A1 | 9/2003 | Hildebrand et al. |
| 2003/0175709 A1 | 9/2003 | Murphy et al. |
| 2003/0177105 A1 | 9/2003 | Xiao et al. |
| 2003/0203370 A1 | 10/2003 | Yakhini et al. |
| 2003/0208454 A1 | 11/2003 | Rienhoff et al. |
| 2003/0224384 A1 | 12/2003 | Sayood et al. |
| 2004/0029264 A1 | 2/2004 | Robbins |
| 2004/0106112 A1 | 6/2004 | Nilsson et al. |
| 2004/0121373 A1 | 6/2004 | Friedlander et al. |
| 2004/0142325 A1 | 7/2004 | Mintz et al. |
| 2004/0152108 A1 | 8/2004 | Keith et al. |
| 2004/0170965 A1 | 9/2004 | Scholl et al. |
| 2004/0171051 A1 | 9/2004 | Holloway |
| 2004/0197813 A1 | 10/2004 | Hoffman et al. |
| 2004/0209299 A1 | 10/2004 | Pinter et al. |
| 2005/0003369 A1 | 1/2005 | Christians et al. |
| 2005/0032095 A1 | 2/2005 | Wigler et al. |
| 2005/0048505 A1 | 3/2005 | Fredrick et al. |
| 2005/0059048 A1 | 3/2005 | Gunderson et al. |
| 2005/0100900 A1 | 5/2005 | Kawashima et al. |
| 2005/0112590 A1 | 5/2005 | Boom et al. |
| 2005/0186589 A1 | 8/2005 | Kowalik et al. |
| 2005/0214811 A1 | 9/2005 | Margulies et al. |
| 2005/0244879 A1 | 11/2005 | Schumm et al. |
| 2005/0272065 A1 | 12/2005 | Lakey et al. |
| 2006/0008824 A1 | 1/2006 | Ronaghi et al. |

(56) References Cited

U.S. PATENT DOCUMENTS

| | | |
|---|---|---|
| 2006/0019304 A1 | 1/2006 | Hardenbol et al. |
| 2006/0024681 A1 | 2/2006 | Smith et al. |
| 2006/0078894 A1 | 4/2006 | Winkler et al. |
| 2006/0133963 A1 | 6/2006 | Stein et al. |
| 2006/0149047 A1 | 7/2006 | Nanduri et al. |
| 2006/0177837 A1 | 8/2006 | Borozan et al. |
| 2006/0183132 A1 | 8/2006 | Fu et al. |
| 2006/0184489 A1 | 8/2006 | Weiner et al. |
| 2006/0192047 A1 | 8/2006 | Goossen |
| 2006/0195269 A1 | 8/2006 | Yeatman et al. |
| 2006/0263789 A1 | 11/2006 | Kincaid |
| 2006/0292585 A1 | 12/2006 | Nautiyal et al. |
| 2006/0292611 A1 | 12/2006 | Berka et al. |
| 2007/0020640 A1 | 1/2007 | McCloskey et al. |
| 2007/0042369 A1 | 2/2007 | Reese et al. |
| 2007/0092883 A1 | 4/2007 | Schouten et al. |
| 2007/0114362 A1 | 5/2007 | Feng et al. |
| 2007/0128624 A1 | 6/2007 | Gormley et al. |
| 2007/0161013 A1 | 7/2007 | Hantash |
| 2007/0162983 A1 | 7/2007 | Hesterkamp et al. |
| 2007/0166705 A1 | 7/2007 | Milton et al. |
| 2007/0225487 A1 | 9/2007 | Nilsson et al. |
| 2007/0238122 A1 | 10/2007 | Allbritton et al. |
| 2007/0244675 A1 | 10/2007 | Shai et al. |
| 2007/0264653 A1 | 11/2007 | Berlin et al. |
| 2008/0003142 A1 | 1/2008 | Link et al. |
| 2008/0076118 A1 | 3/2008 | Tooke et al. |
| 2008/0081330 A1 | 4/2008 | Kahvejian |
| 2008/0085836 A1 | 4/2008 | Kearns et al. |
| 2008/0090239 A1 | 4/2008 | Shoemaker et al. |
| 2008/0176209 A1 | 7/2008 | Muller et al. |
| 2008/0269068 A1 | 10/2008 | Church et al. |
| 2008/0280955 A1 | 11/2008 | McCarnish |
| 2008/0292506 A1 | 11/2008 | Itoh |
| 2008/0293589 A1 | 11/2008 | Shapero |
| 2009/0009904 A1 | 1/2009 | Yasuna et al. |
| 2009/0019156 A1 | 1/2009 | Mo et al. |
| 2009/0026082 A1 | 1/2009 | Rothberg et al. |
| 2009/0029385 A1 | 1/2009 | Christians et al. |
| 2009/0042206 A1 | 2/2009 | Schneider et al. |
| 2009/0098551 A1 | 4/2009 | Landers et al. |
| 2009/0099041 A1 | 4/2009 | Church et al. |
| 2009/0105081 A1 | 4/2009 | Rodesch et al. |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce et al. |
| 2009/0163366 A1 | 6/2009 | Nickerson et al. |
| 2009/0181389 A1 | 7/2009 | Li et al. |
| 2009/0191565 A1 | 7/2009 | Lapidus et al. |
| 2009/0192047 A1 | 7/2009 | Parr et al. |
| 2009/0202984 A1 | 8/2009 | Cantor |
| 2009/0203014 A1 | 8/2009 | Wu et al. |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0301382 A1 | 12/2009 | Patel |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0086926 A1 | 4/2010 | Craig et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0143908 A1 | 6/2010 | Gillevet |
| 2010/0159440 A1 | 6/2010 | Messier et al. |
| 2010/0188073 A1 | 7/2010 | Rothberg et al. |
| 2010/0196911 A1 | 8/2010 | Hoffman et al. |
| 2010/0197507 A1 | 8/2010 | Rothberg et al. |
| 2010/0216151 A1 | 8/2010 | Lapidus et al. |
| 2010/0216153 A1 | 8/2010 | Lapidus et al. |
| 2010/0248984 A1 | 9/2010 | Shaffer et al. |
| 2010/0282617 A1 | 11/2010 | Rothberg et al. |
| 2010/0285578 A1 | 11/2010 | Selden et al. |
| 2010/0297626 A1 | 11/2010 | McKernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0311061 A1 | 12/2010 | Korlach et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |
| 2011/0053208 A1 | 3/2011 | Reiss et al. |
| 2011/0092375 A1 | 4/2011 | Zamore et al. |
| 2011/0098193 A1 | 4/2011 | Kingsmore et al. |
| 2011/0117544 A1 | 5/2011 | Lexow |
| 2011/0118145 A1 | 5/2011 | Akmaev et al. |
| 2011/0159499 A1 | 6/2011 | Hindson et al. |
| 2011/0166029 A1 | 7/2011 | Margulies et al. |
| 2011/0224105 A1 | 9/2011 | Kum et al. |
| 2011/0230365 A1 | 9/2011 | Rohlfs et al. |
| 2011/0257889 A1 | 10/2011 | Klammer et al. |
| 2011/0288780 A1 | 11/2011 | Rabinowitz et al. |
| 2011/0301042 A1 | 12/2011 | Steinmann et al. |
| 2012/0015050 A1 | 1/2012 | Abkevich et al. |
| 2012/0021930 A1 | 1/2012 | Schoen et al. |
| 2012/0046877 A1 | 2/2012 | Hyland et al. |
| 2012/0059594 A1 | 3/2012 | Hatchwell et al. |
| 2012/0074925 A1 | 3/2012 | Oliver |
| 2012/0079980 A1 | 4/2012 | Taylor et al. |
| 2012/0115736 A1 | 5/2012 | Bjornson et al. |
| 2012/0164630 A1 | 6/2012 | Porreca et al. |
| 2012/0165202 A1 | 6/2012 | Porreca et al. |
| 2012/0179384 A1 | 7/2012 | Kuramitsu et al. |
| 2012/0214678 A1 | 8/2012 | Rava et al. |
| 2012/0216151 A1 | 8/2012 | Sarkar et al. |
| 2012/0220478 A1 | 8/2012 | Shaffer |
| 2012/0236861 A1 | 9/2012 | Ganeshalingam et al. |
| 2012/0245041 A1 | 9/2012 | Brenner et al. |
| 2012/0252020 A1 | 10/2012 | Shuber |
| 2012/0252684 A1 | 10/2012 | Selifonov et al. |
| 2012/0258461 A1 | 10/2012 | Weisbart |
| 2012/0270212 A1 | 10/2012 | Rabinowitz et al. |
| 2012/0270739 A1 | 10/2012 | Rava et al. |
| 2013/0040824 A1 | 2/2013 | Lo et al. |
| 2013/0082082 A1 | 4/2013 | Vermeesch et al. |
| 2013/0130921 A1 | 5/2013 | Gao et al. |
| 2013/0178378 A1 | 7/2013 | Hatch et al. |
| 2013/0183672 A1 | 7/2013 | de Laat et al. |
| 2013/0222388 A1 | 8/2013 | McDonald |
| 2013/0268474 A1 | 10/2013 | Nizzari et al. |
| 2013/0275103 A1 | 10/2013 | Struble et al. |
| 2013/0288242 A1 | 10/2013 | Stoughton et al. |
| 2013/0323730 A1 | 12/2013 | Curry et al. |
| 2013/0332081 A1 | 12/2013 | Reese et al. |
| 2013/0344096 A1 | 12/2013 | Chiang et al. |
| 2014/0059083 A1 | 2/2014 | Adams et al. |
| 2014/0129201 A1 | 5/2014 | Kennedy et al. |
| 2014/0136120 A1 | 5/2014 | Colwell et al. |
| 2014/0206552 A1 | 7/2014 | Rabinowitz et al. |
| 2014/0222349 A1 | 8/2014 | Higgins et al. |
| 2014/0228226 A1 | 8/2014 | Yin et al. |
| 2014/0280327 A1* | 9/2014 | Pham .................. G16B 30/00 707/770 |
| 2014/0314638 A1 | 10/2014 | Taunk |
| 2014/0318274 A1 | 10/2014 | Zimmerman et al. |
| 2014/0342354 A1 | 11/2014 | Evans et al. |
| 2014/0361022 A1 | 12/2014 | Finneran |
| 2015/0051085 A1 | 2/2015 | Vogelstein et al. |
| 2015/0056613 A1 | 2/2015 | Kural |
| 2015/0178445 A1 | 6/2015 | Cibulskis et al. |
| 2015/0299767 A1 | 10/2015 | Armour et al. |
| 2016/0034638 A1 | 2/2016 | Spence et al. |
| 2016/0048608 A1 | 2/2016 | Frieden et al. |
| 2016/0210486 A1 | 7/2016 | Porreca et al. |

(56) References Cited

U.S. PATENT DOCUMENTS

| | | |
|---|---|---|
| 2017/0044610 A1 | 2/2017 | Johnson |
| 2017/0129964 A1 | 5/2017 | Cheung |

FOREIGN PATENT DOCUMENTS

| | | |
|---|---|---|
| EP | 10770071.8 | 11/2010 |
| EP | 2425240 A2 | 3/2012 |
| EP | 2437191 A2 | 4/2012 |
| EP | 2716766 A1 | 4/2014 |
| WO | WO 95/011995 A1 | 5/1995 |
| WO | WO 96/019586 A1 | 6/1996 |
| WO | WO 98/014275 A1 | 4/1998 |
| WO | WO 98/044151 A1 | 10/1998 |
| WO | WO 00/018957 A1 | 4/2000 |
| WO | WO 02/093453 A2 | 11/2002 |
| WO | WO 2004/015609 A2 | 2/2004 |
| WO | WO 2004/018497 A2 | 3/2004 |
| WO | WO 2004/083819 A2 | 9/2004 |
| WO | WO 2005/003304 A2 | 1/2005 |
| WO | WO 2007/010251 A2 | 1/2007 |
| WO | WO 2007/107717 A1 | 9/2007 |
| WO | WO 2007/123744 A2 | 11/2007 |
| WO | WO 2007/135368 A2 | 11/2007 |
| WO | WO 2008/067551 A2 | 6/2008 |
| WO | WO 2009/036525 A2 | 3/2009 |
| WO | WO 2010/024894 A1 | 3/2010 |
| WO | WO 2010/126614 A2 | 11/2010 |
| WO | WO 2011/006020 A1 | 1/2011 |
| WO | WO 2011/102998 A2 | 8/2011 |
| WO | WO 2011/006291 A2 | 12/2011 |
| WO | WO 2012/006291 A2 | 1/2012 |
| WO | WO 2012/040387 A1 | 3/2012 |
| WO | WO 2012/087736 A1 | 6/2012 |
| WO | WO 2012/109500 A2 | 8/2012 |
| WO | WO 2012/134884 A1 | 10/2012 |
| WO | WO 2012/149171 A1 | 11/2012 |
| WO | WO 2012/170725 A2 | 12/2012 |
| WO | WO 2013/05257 A2 | 4/2013 |
| WO | WO 2013/052913 A2 | 4/2013 |
| WO | WO 2013/058907 A1 | 4/2013 |
| WO | WO 2013/148496 A1 | 10/2013 |
| WO | WO 2013/177086 A1 | 11/2013 |
| WO | WO 2013/191775 A2 | 12/2013 |
| WO | WO 2014/074246 A1 | 5/2014 |
| WO | WO 2014/116881 A1 | 7/2014 |
| WO | WO 2015/089333 A1 | 6/2015 |

OTHER PUBLICATIONS

Beer, 1962, Determination of base sequence in nucleic acids with the electron microscope: visibility of a marker, PNAS 48(3):409-416.
Bolstad, 2003, A comparison of normalization methods for high density oligonucleotide array data based on variance and bias, Bioinformatics 19(2):185-193.
Bonfield, 2013, Compression of FASTQ and SAM format sequencing data, PLoS One 8(3):e59190.
Bose, 2012, BIND-An algorithm for loss-less compression of nucleotide sequence data, J Biosci 37(4):785-789.
Brezina, 2010, Single-gene testing combined iwth single nucleotide polymorphism microarray preimplantatoin genetic diagnosis for aneuploidy, Fert Siert 95(5):1786e5-e8.
Brinkman, 2004, Splice Variants as Cancer Biomarkers, Clin Biochem 37:584.
Bullard, 2010, Evaluation of statistical methods for normalization and differential expression in mRNA-Seq experiments, BMC Bioinformatics 11 (1):94.
Carpenter, 2013, Pulling out the 1 %: whole-genome capture for the targeted enrichment of ancient DNA sequencing libraries, Am J Hum Genet 93(5):852-864.
Caruthers, 1985, Gene synthesis machines: DNA chemistry and its uses, Science 230:281-285.

CDC, 2011 Assisted Reproductive Technology: Fertility Clinic Success Rates Report.
Challis, 2012, An integrative variant analysis suite for whole exome next-generation sequencing data, BMC Informatics 13{8):1-12.
Chen, 2010, Identification of racehorse and sample contamination by novel 24-plex STR system, Forensic Sci Int: Genetics 4:158-167.
Cremers, 1998, Autosomal Recessive Retinitis Pigmentosa and Cone-Rod Dystrophy Caused by Splice Site Mutations in the Stargardt's Disease Gene ABCR, Hum Mol Gen 7(3):355.
Cronin, 1996, Cystic Fibrosis Mutation Detection by Hybridization to Light-Generated DNA Probe Arrays Human Mutation 7:244.
Peng et al., 2012, Supplementary Material, Nature Biotechnology, S1-1-S1-1 1, Retrieved from the Internet on Oct. 24, 2012.
Deorowicz, 2013, Data compression for sequencing data, Alg for Mole Bio 8:25.
Diep, 2012, Library-free methylation sequencing with bisulfite padlock probes, Nature Methods 9:270-272 (and supplemental information).
Dolinsek, 2013, Depletion of unwanted nucleic acid templates by selection cleavage: LNAzymes, catalytically active Dligonucleotides containing locked nucleic acids, open a new window for detecting rare microbial community members, APP Env Microbiol 79(5):1534-1544.
Drmanac, 1992, Sequencing by hybridization: towards an automated sequencing of one million M13 clones arrayed on membranes, Elctrophoresis 13:566-573.
Ericsson, 2008, A dual-tag microarray platform for high-performance nucleic acid and protein analyses, Nucl Acids Res B6:e45.
Faust, 2014, SAMBLASTER: fast duplicate marking and structural variant read extraction, Bioinformatics published online May 7, 2014.
Giusti, 1993, Synthesis and Characterization off-Fluorescent-dye-labeled Oligonucleotides, PCR Meth Appl 2:223-227.
Green, 2005, Suicide polymerase endonuclease restriction, a novel technique for enhancing PCR amplification of minor DNA template, Appl Env Microbiol 71 (8):4721-4727.
Guerrero-Fernandez, 2013, FQbin: a compatible and optimize dformat for storing and managing sequence data, WBBIO Proceedings, Granada 337-344.
Gupta, 1991, A general method for the synthesis of 3'-sulfhydryl and phosphate group containing oligonucleotides, Nucl Acids Res 19(11):3019-3025.
Harris, 2008, Helicos True Single Molecule Sequencing (tSMS) Science 320:106-109.
Heger, 2006, Protonation of Cresol Red in Acidic Aqueous Solutions Caused by Freezing, J Phys Chem B 110 (3):1277-1287.
Heid, 1996, Real time quantitative PCR, Genome Res 6:986-994.
Homer et al., 2008, Resolving Individuals Contributing Trace Amounts of DNA to Highly Complex Mixtures Using High-Density SNP Genotyping Microarrays. PLoS One 4(8):e1000167.
Homer, 2009, BF AST: An alignment tool for large scale genome resequencing, PLoS ONE 4(11 ):e 7767.
Housley, 2009, SNP discovery and haplotype analysis in the segmentally duplicated DRD5 coding region, Ann Hum Genet 73(3):274-282.
llumina, 2010, De Novo assembly using Illumina reads, Technical Note (8 pages).
International Human Genome Sequencing Consortium, 2004, Finishing the euchromatic sequence of the human genome, Nature 431:931-945.
International Search Report and Written Opinion Jan. 29, 2015, for PCT/US2014/060056, filed Oct. 10, 2014 (10 pages).
International Search Report and Written Opinion mailed Dec. 2, 2015, for International Patent Application No. PCT/US2015/049132 with Internaional Filing Date Sep. 9, 2015 (14 pages).
International Search Report and Written Opinion mailed Dec. 9, 2014, for International Patent Application No. PCT/US14/28212, filed Mar. 14, 2014 (11 pages).
International Search Report and Written Opinion mailed Jan. 22, 2016, for International Patent Application No. PCT/US2015/050964, filed Sep. 18, 2015 (6 pages).

(56) References Cited

OTHER PUBLICATIONS

International Search Report and Written Opinion mailed Jan. 7, 2015, for International Patent Application No. PCT/US14/60256, filed Oct. 13, 2014 (9 pages).
International Search Report and Written Opinion mailed May 4, 2016, for International patent application No. PCT/US2016/012886 with international filing date Jan. 6, 2015 (7 pages).
International Search Report and Written Opinion mailed on Jan. 29, 2015, for Patent Application No. PCT/US14/61138, filed Oct. 17, 2014, (11 pages).
International Search Report and Written Opinion mailed on Jun. 28, 2013, for Patent Application No. PCT/US2013/032885, filed Mar. 19, 2013, (9 pages).
International Search Report and Written Opinion mailed on Mar. 18, 2015, for Patent Application No. PCT/US14/40516, filed Jun. 2, 2014 (16 pages).
International Search Report and Written Opinion mailed on May 2, 2016, for International Patent Application No. PCT/US2016/013346, filed Jan. 14, 2016 (7 pages).
International Search Report and Written Opinion mailed Sep. 2, 2015 for International Patent Application No. PCT/US2015/030366, filed May 12, 2015 (12 pages).
Isosomppi, 2009, Disease-causing mutations in the CLRNI gene alter normal CLRN1 protien trafficking to the plasma membrane, Mol Vis 15:1806-1818.
Kambara et al., Optimization of Parameters in a DNA Sequenator Using Fluorescence Detection, Nature Biotechnology 6:816-821 (1988).
Kerem, 1989, Identification of the cystic fibrosis gene: genetic analysis, Science 245:1073-1080.
Kinde, 2012, FAST-SeqS: a simple an effective method for detection of aneuploidy by massively parallel sequencing, PLoS One 7(7):e41162.
Li, 2003, DNA binding and cleavage by the periplasmic nuclease Vvn: a novel structure with a known active site, EMBO J 22(15):4014-4025.
Li, 2010, Fast and accurate long-read alignment with Burrows-Wheeler transform, Bioinformatics 26(5):589-95.
Li, 2012, A new approach to detecting low-level mutations in next-generation sequence data, Genome Biol 13:1-15.
Li, 2014, HUGO: Hierarchical multi-reference Genome compression for aligned reads, JAMIA 21:363-373.
Lin, 2010, A molecular inversion prove assay for detecting alternative splicing, BMC Genomics 11(712):1-14.
Liu, 2012, Comparison of next-generation sequencing systems, J Biomed Biotech 2012:251364.
Ma, 2006, Application of real-time polymerase chain reaction (RT-PCR), J Am Soc 1-15.
McKenna, 2010, The Genome Analysis Toolkit: A MapReduce framework for analyzing next-generation DNA sequencing data, Genome Research 20:1297-1303.
Meyer, 2007, Targeted high-throughput sequencing of tagged nucleic acid samples, Nucleic Acids Research 35(15): e97 (5 pages).
Miesenbock, 1998, Visualizing secretion and synaptic transmission with pH-sensitive green fluorescent proteins, Nature 394(6689):192-95.
Miller, 2010, Assembly algorithms for next-generation sequencing data, Genomics 95:315-327.
Miner, 2004, Molecular barcodes detect redundancy and contamination in hairpin-bisulfite PCR, Nucl Acids Res 32 (17):e135.
Mohammed, 2012, DELIMINATE-a fast and efficient methods for loss-less compression of genomice sequences, Bioinformatics 28(19):2527-2529.
Munne, 2012, Preimplantation genetic diagnosis for aneuploidy and translocations using array comparative genomic hybridization, Curr Genomics 13(6):463-470.
Nelson, 1989, Bifunctional oligonucleotide probes synthesized using a novel CPG support are able to detect single pase pair mutations, Nucl Acids Res 17(18):7187-7194.

Nuttle, 2013, Rapid and accurate large-scale genotyping of duplicated genes and discovery of interlocus gene conversions, Nat Meth 10(9):903-909.
O'Roak, 2012, Multiplex targeted sequencing identifies recurrently mutated genes in autism spectrum disorders, Science 338(6114):1619-1622.
Parkinson, 2012, Preparation of high-quality next-generation sequencing libraries from picogram quantities of target DNA, Genome Res 22:125-133.
Pastor, 2010, Conceptual modeling of human genome mutations: a dichotomy between what we have and what we should have, 2010 Proc BIOSTEC Bioinformatics, pp. 160-166.
Paton, 2000, Conceptual modelling of genomic information, Bioinformatics 16(6):548-57.
Pertea et al., 2003, TIGR Gene indices clustering tools (TGICL): a software system for fast clustering of large EST datasets, Bioinformatics 19(5):651-52.
Pinho, 2013, MFCompress: a compression tool for FAST A and multi-FAST A data, Bioinformatics 30(1):117-8.
Qiagen, 2011, Gentra Puregene handbook, 3d Ed. (72 pages).
Saihan, 2009, Update on Usher syndrome, Cur Op Neurology 22:19-27.
Schneeberger, 2011, Reference-guided assembly of four diverse *Arabidopsis thaliana* genomes, PNAS 108 (25):10249-10254.
Schoolcraft, 2010, Clinical application of comprehensive chromosomal screening at the blastocyst stage, Fert Steril 94 (5):1700-1706.
Schouten, 2002, Relative Quantification of 40 Nucleic Acid Sequences by Multiplex Ligation-Dependent Probe Amplification, Nucle Acids Res 30 (12):257.
Shen, 2013, Multiplex capture with double-stranded DNA probes, Genome Medicine 5(50):1-8.
Shendure, 2008, Next-generation DNA sequencing, Nat Biotech 26(10):1135-1145.
Smith, 1985, The synthesis of oligonucleotides containing an aliphatic amino group at the 5' terminus: synthesis of fluorescent DNA primers for use in DNA sequence analysis, Nucl. Acid Res., 13:2399-2412.
Smith, 2010, Highly-multiplexed barcode sequencing: an efficient method for parallel analysis of pooled samples, Nucleic Acids Research 38{13):e142 {8 pages).
Sproat, 1987, The synthesis of protected 5'-mercapto-2',5'-dideoxyribonucleoside-3'-O-phosphoramidites; uses of 5'-mercapto-oligodeoxyribonucleotides, Nucl Acid Res 15:4837-4848.
Summerer, 2010, Targeted High Throughput Sequencing of a Cancer-Related Exome Subset by Specific Sequence Capture With a Fully Automated Microarray Platform, Genomics 95(4):241-246.
Iran, 2014, Clinical outcome of preimplantation genetic diagnosis and screening using next generation sequencing, GigaScience 3(30):1-9.
lrhiyagarajan, 2006, PathogenMIPer: a tool for the design of molecular inversion probes to detect multiple pathogens, BMC Bioinformatics 7:500.
lrkachuk, 1990, Detection of bcr-abl Fusion in Chronic Myelogeneous Leukemia by in Situ Hybridization, Science 250:559.
lrobler, 2005, The SNPlex Genotyping System: A Flexible and Scalable Platform for SNP Genotyping, J Biomol Tech 16{4):398.
Veeneman, 2012, Oculus: faster sequence alignment by streaming read compression, BMC Bioinformatics 13:297.
Wagle, 2012, High-throughput detection of actionable genomic alterations in clinical tumor samples by targeted massively parallel sequencing, Cancer Discovery 2:82-93.
Wang, 2012, Molecular inversion probes: a novel microarray technology and its application in cancer research, Cancer Genetics 205:341-355.
Waszak, 2010, Systematic inference of copy-number genotypes from personal genome sequencing data reveals extensive olfactory gene content diversity, PLoS Comp Biol 6(11 ):e1000988.
Xu, 2012, FastUniq: A fast de novo duplicates removal tool for paired short reads, PLoS One 7(12):e52249.
Yershov, 1996, DNA analysis and diagnostics on oligonucleotide microchips, PNAS 93:4913-4918.

(56) References Cited

OTHER PUBLICATIONS

Yoon, 2014, MicroDuMIP: target-enrichment technique for microarray-based duplex molecular inversion probes, Nucl Ac Res 43{5}:e28.
Zhou, 2014, Bias from removing read duplication in ultra-deep sequencing experiments, Bioinformatics 30 (8):1073-1080.
Zuckerman, 1987, Efficient methods for attachment of thiol specific probes to the 3'—ends of synthetic oligodeoxyribonucleotides, Nucl Acid Res 15(13):5305-5321.
Lam, et al., 2008, Compressed indexing and local alignment of DNA, Bioinformatics 24(6):791-97.
Langmead, et al., 2009, Ultrafast and memory-efficient alignment of short DNA sequences to the human genome, Genome Biology, 10:R25.
Larkin M.A., et al., 2007, Clustal Wand Clustal X version 2.0, Bioinformatics, 23, 2947-2948.
Lecompte, O., et al., 2001, Multiple alignment of complete sequences (MACS) in the post-genomic era, Gene 270:17-30.
Li & Durbin, 2009, Fast and accurate short read alignment with Burrows-Wheeler transform, Bioinformatics, 25 (14):1754-60.
Li, et al., 2008, SOAP: short oligonucleotide alignment program, Bioinformatics 24(5):713-14.
Li, et al., 2009, SOAP2: an improved ultrafast tool for short read alignment, Bioinformatics 25(15): 1966-67.
Li, et al., 2009, The Sequence Alignment/Map format and SAMtools, Bioinformatics, 2009, 25(16):2078-9.
Li, et al., 2011, Single Nucleotide Polymorphism Genotyping and Point Mutation Detection by Ligation on Microarrays, Journal of Nanoscience and Nanotechnology 11(2): 994-1003.
Lin, et al., 2012, Development and evaluation of a reverse dot blot assay for the simultaneous detection of common alpha and beta thalassemia in Chinese, Blood Cells Molecules, and Diseases 48(2): 86-90.
Lipman, D.J., et al., 1985, Rapid and sensitive protein similarity searches, Science 227(4693):1435-41.
Mamanova, 2010, Target-enrichment strategies for nextgeneration sequencing, Nature Methods 7(2):111-8.
Margulies, et al., 2005, Genome sequencing in microfabricated high-density picolitre reactors, Nature 437:376-380.
Marras, 1999, Multiplex detection of single-nucleotide variations using molecular beacons, Genetic Analysis: Biomolecular Engineering 14:151.
May, Robert M., 1988, How Many Species Are There on Earth?, Science 241 :1441.
Mills, RE., et al., 2010, Mapping copy number variation by population-scale genome sequencing, Nature 470:59-65.
Minton, et al., 2011, Mutation Surveyor: Software for DNA Sequence Analysis, Methods in Molecular Biology 688:143-53.
Mockler, et al., 2005, Applications of DNA tiling arrays for whole-genome analysis, Genomics 85:1-15.
Moudrianakis, E. N. & Beer M., 1965, Base sequence determination in nucleic acids with the electron microscope, PNAS, 53:564-71.
Mullan, L. J., 2002, Multiple sequence alignment-the gateway to further analysis, Brief Bioinform., 3:303-5.
Nan, et al., 2006, A novel CFTR mutation found in a Chinese patient with cystic fibrosis, Chinese Medical Journal 119(2):103-9.
Narang, et al., 1979, Improved phosphotriester method for the synthesis of gene fragments, Methods Enzymol., 68:90.
Ng, et al., 2009, Targeted capture and massively parallel sequencing of 12 human exomes, Nature 461 (7261):272-6.
Nicholas, H. B. Jr., et al., 2002, Strategies for multiple sequence alignment, Biotechniques 32:572-91.
Nickerson, et al., 1990, Automated DNA diagnostics using an ELISA-based oligonucleotide ligation assay, Proc. National Academy of Science 87:8923-7.
Nielsen, et al., 1999, Peptide Nucleic Acids, Protocols and Applications (Norfolk: Horizon Scientific Press, 1-19).
Nilsson, et al., 2006, Analyzing genes using closing and replicating circles, Trends in Biotechnology 24:83-8.
Ning, Z., et al., 2001, SSAHA: a fast search method for large DNA databases, Genome Research 11(10): 1725-9 (2001).
Oka et al., 2006, Detection of loss of heterozygosity in the p53 gene in renal cell carcinoma and bladder cancer using the polymerase chain reaction, Molecular Carcinogenesis 4(1):10-13.
Oliphant, et al., 2002, BeadArray?Technology : Enabling an Accurate, Cost-Effective Approach to High-Throughput Genotyping, Biotechniques Suppl:56-8, 60-1.
Ostrer, et al., 2001, A genetic profile of contemporary Jewish populations, Nature Reviews Cancer 2:891-8.
Parameswaran, et al., 2007, A pyrosequencing-tailired nucleotide barcode design unveils opportunities for large-scale sample multiplexing, Nucleic Acids Research 35:e130, pp. 1-9.
Pearson W.R., et al., 1988, Improved tools for biological sequence comparison, PNAS 85(8):2444-8.
Pertea, et al., 2003, TIGR gene indices clustering tools (TGICL), Bioinformatics 19(5):651-52.
Procter, et al., 2006, Molecular Diagnosis of Prader-Willi and Angelman Syndromes~ Methylation-Specific Melting Analysis and Methylation-Specific Multiplex Ligation-Dependent Probe Amplification, linical Chemistry 52(7):1276-83.
Quail, et al., 2010, DNA: Mechanical Breakage, Encyclopedia of Life Sciences 2010.
Rambaut, et al., 1997, Seq-Gen:an application for the Monte Carlo simulation of DNA sequence evolution along phylogenetic trees, Bioinformatics (formerly CABIOS) 13:235-38.
Richter, et al., 2008, MetaSim-A Sequencing Simulator for Genomics and Metagenomics, PLOS ONE 3:e3373.
Rosendahl, et al., 2013, CFTR, SPINK1, CTRC and PRSSI variants in chronic pancreatitis: is the role of mutated CFTR overestimated?, Gut 62:582-592.
Rothberg, et al., 2011, An integrated semiconductor device enabling non-optical genome sequencing, Nature 475:348-52.
Rowntree and Harris, 2003, The phenotypic consequences of CFTR mutations, Ann Hum Gen 67:471-485.
Sanger et al., 1977, DNA Sequencing with chain-terminating inhibitors, PNAS 74(12):5463-5467.
Santa Lucia, John Jr., 1998, A unified view of polymer, dumbbell, and oligonucleotide DNA nearest-neighbor thermodynamics, Proc. National Academy of Science USA 95:1460-5.
Sargent, T.D., 1988, Isolation of Differentially Expressed Genes, Methods in Enzymology 152:432.
Sauro, 2004, How Do You Calculate a Z-Score/ Sigma Level?, https://www.measuringusability.com/zcalc.htm (online publication).
Sauro, 2004, What's a Z-Score and Why Use it in Usability Testing?, https://www.measuringusability.com/z.htm (online publication).
Schadt, et al., 2010, A window into third-generation sequencing, Human Molecular Genetics 19(R2):R227-40.
Schatz, et al., 2010, Assembly of large genomes using second-generation sequencing, Genome Res., 20:1165-1173.
Schrijver, 2005, Diagnostic testing by CFTR gene mutation analysis in a large group of Hispanics, J Mol Diag 7(2):289-299.
Schwartz, et al., 2009, Identification of Cystic Fibrosis Variants by Polymerase Chain Reaction/Oligonucleotide Ligation Assay, The Journal of Molecular Diagnostics 11 (3):211-15.
Gut & Beck, 2995, A procedure for selective DNA alkylation and detection by mass spectrometry, Nucl Acids Res 23 (8):1367-1373.
Hammond et al., 1996, Extraction of DNA from preserved animal specimens for use in randomly amplified polymorphic DNA analysis, An Biochem 240:298-300.
Hardenbol et al., 2005, Highly multiplexed molecular inversion probe genotyping: over 10,000 targeted SNPs genotyped in a single tube assay, Genome Res 15:269-75.
Kennedy et al., 2013, Accessing more human genetic variation with short sequencing reads, American Society of Human Genetics 63rd Annual Meeting, Abstract, Oct. 22, 2013 (2 pages).
Kirpekar et al., 1994, Matrix assisted laser desorption/ionization mass spectrometry of enzymatically synthesized RNA up to 150 kDa, Nucleic Acids Res 22:3866-3870.
Klein, et al., 2011,LOCAS-A low coverage sequence assembly tool for re-sequencing projects, PLoS One 6(8) article 2455.

(56) References Cited

OTHER PUBLICATIONS

Krishnakumar et al., 2008, A comprehensive assay for targeted multiplex amplification of human DNA sequences, DNAS 105:9296-301.

Maxam & Gilbert, 1977, A new method for sequencing DNA, PNAS 74:560-564.

Non-final Office Action mailed Mar. 12, 2014, for U.S. Appl. No. 14/132,364, filed Dec. 18, 2013 (8 pages).

Nordhoff et al., 1993, Ion stability of nucleic acids in infrared matrix-assisted laser desorption/ ionization mass spectrometry, Nucl Acid Res 21(15):3347-57.

Oefner et al., 1996, Efficient random sub-cloning of DNA sheared in a recirculating point-sink flow system, Nucleic Acids Res 24(20):3879-3886.

Alazard et al., 2002, Sequencing of production-scale synthetic oligonucleotides by enriching for coupling failures using matrix-assisted laser desorption/ ionization time-of-flight mass spectrometry, Analytical biochemistry 301 :57-64.

Aljanabi and Martinez, 1997, Universal and rapid salt-extraction of high quality genomic DNA for PCR-based techniques, Nucl. Acids Res 25:4692-4693.

Bentzley et al., 1996, Oligonucleotide sequence and composition detenrnined by matrix-assisted laser desorption/ionization, Anal Chem 68:2141-2146.

Bentzley et al., 1998, Base specificity of oligonucleotide digestion by calf spleen phosphodiesterase with matrix-assisted laser desorption ionization analysis, Anal Biochem 258:31-37.

Boyden, 2013, High-throughput screening for SMN1 copy number loss by next-generation sequencing, American Society of Human Genetics, 63rd Annual Meeting, Abstract, Oct. 22, 2013 (2 pages).

Boyer, 1971, DNA restriction and modification mechanisms in bacteria, Ann Rev Microbiol 25:153-76.

Browne, 2002, Metal ion-catalyzed nucleic Acid alkylation and fragmentation, J Am Chem Soc 124(27):7950-7962.

Chan et al., 2011, Natural and engineered nicking endonucleases-from cleavage mechanism to engineering of strand-specificity, Nucl Acids Res 39(1):1-18.

Chennagiri, 2013, A generalized scalable database model for storing and exploring genetic variations detected using sequencing data, American Society of Human Genetics 63rd Annual Meeting, Abstract, Oct. 22, 2013 (2 pages).

Faulstich et al., 1997, A sequencing method for RNA oligonucleotides based on mass spectrometry, Anal Chem 59:4349-4353.

Glover et al., 1995, Sequencing of oligonucleotides using high performance liquid chromatography and electrospray mass spectrometry, Rapid Com Mass Spec, 9:897-901.

Umbarger et al., 2013, Detecting contamination in Next Generation DNA sequencing libraries, American Society of Human Genetics 63rd Annual Meeting, Abstract, Oct. 22, 2013 (2 pages).

Nallace & Miyada, 1987, Oligonucleotide probes for the screening of recombinant DNA libraries, Methods Enzymol 152:432-442.

Wu & Aboleneen, 2001, Improved oligonucleotide sequencing by alkaline phosphatase and exonuclease digestions vith mass spectrometry, Anal Chem 290:347-352.

Wu et al., 1998, Sequencing regular and labeled oligonucleotides using enzymatic digestion and ionspray mass spectrometry, Anal Biochem 263:129-138.

Yuan, 1981, Structure and mechanism of multifunctional restriction endonucleases, Ann Rev Biochem 50:285-319.

Akhras, M.S., et al., 2007, Connector Inversion Probe Technology: A Powerful OnePrimer Multiplex DNA Amplification System for Numerous Scientific Applications PLOS ONE 2{9}:e915.

Albert, 2007, Direct selection of human genomic loci by microarray hybridization, Nature Methods 4(11):903-5.

Antonarakis and the Nomenclature Working Group, 1998, Recommendations for a nomenclature system for human gene mutations, Human Mutation 11:1-3.

Ball, M.P., et al., 2009, Targeted and genome-scale strategies reveal gene-body methylation signatures in human cells, Nature Biotechnology, 27:361-8.

Barany, F, 1991, Genetic disease detection and DNA amplification using cloned thermostable ligase, PNAS, 88:189-193.

Barany, F, 1991, The Ligase Chain Reaction in a PCR World, Genome Research, 1:5-16.

Ordahl et al., 1976, Sheared DNA fragment sizing: comparison of techniques, Nucleic Acids Res 3:2985-2999.

Owens et al., 1998, Aspects of oligonucleotide and peptide sequencing with MALDI and electrospray mass spectrometry, Bioorg Med Chem 6:1547-1554.

Pieles et al., 1993, Matrix-assisted laser desorption ionization time—0f-flight mass spectrometry: A powerful tool for the mass and sequence analysis of natural and modified oligonucleotides, Nucleic Acids Res 21 :3191-3196.

Porreca et al., 2007, Multiplex amplification of large sets of human exons, Nat Methods 4:931-6.

Porreca et al., 2013, Analytical performance of a Next-Generation DNA sequencing-based clinical workflow for genetic carrier screening, American Society of Human Genetics 63rd Annual Meeting, Abstract, Oct. 22, 2013 (2 pages).

Roberts, 1980, Restriction and modification enzymes and their recognition sequences, Nucleic Acids Res 8(1 ):r63-r80.

Schuette et al., 1995, Sequence analysis of phosphorothioate oligonucleotides via matrix-assisted laser desorption ionization time—0f-flight mass spectrometry, J. Pharm. Biomed. Anal 13:1195-1203.

Smirnov et al., 1996, Sequencing oligonucleotides by exonuclease digestion and delayed extraction matrix-assisted laser desorption ionization time-of-flight mass spectrometry, Anal Biochem 238:19-25.

Sunnucks et al., 1996, Microsatellite and chromosome evolution of parthenogenetic sitobion aphids in Australia, Genetics 144:747-756.

Thorstenson, et al., 1998 An automated hydrodynamic process for controlled, unbiased DNA shearing, Genome Res g:848-855.

Turner et al., 2009, Massively parallel exon capture and library-free resequencing across 16 genomes, Nature Methods 6:315-316, and Supplementary Materials (14 pages).

Bau, et al., 2008, Targeted next-generation sequencing by specific capture of multiple genomic loci using low-volume microfluidic DNA arrays, Analytical and bioanalytical chem 393(1):171-5.

Benner, et al., 2001, Evolution, language and analogy in functional genomics, Trends in Genetics 17:414-8.

Braasch, et al., 2001, Locked nucleic acid (LNA): ¢ne-tuning the recognition of DNA and RNA, Chemistry & Biology 8 (1):1-7.

Braslavsky, et al., 2003, Sequence information can be obtained from single DNA molecules, Proceedings of the National Academy of Sciences, (USA) 100:3960-4.

Brown, et al., 1979, Chemical synthesis and cloning of a tyrosine tRNA gene, Methods Enzymol., 68:109.

Furtado et al., 2011, Characterization of large genomic deletions in the FBN1 gene using multiplex ligation-dependent probe amplification, BMC Medical Genetics 12:119 (7 pages).

Bell et al., 2011, Carrier testing for severe childhood recessive diseases by next-generation sequencing, Science Translational Medicine 3 {65ra4), 15 pages.

Garber, 2008, Fixing the front end, Nature Biotechnology 26(10):1101-04.

Nuttle et al., 2014, Resolving genomic disorder-associated breakpoints within segmental DNA duplications using massively parallel sequencing, Nature Protocols 9(6):1496-1513.

Hiatt et al., 2013, Single molecule molecular inversion probes for targeted, high-accuracy detection of low-frequency variation, Genome Research 23:843-54.

Miyazaki et al., 2009, Characterization of deletion breakpoints in patients with dystrophinopathy carrying a deletion of exons 45-55 of the Duchenne muscular dystrophy {DMD) gene, Journal of Human Genetics 54:127-30.

Olkoniewski et al., 2013, Precise breakpoint localization of large genomic deletions using PacBio and Illumina next-Generation sequencers, Biotechniques 54(2):98-100.

Schiffman, 2009, Molecular inversion probes reveal patterns of 9p21 deletion and copy number aberrations in childhood leukemia, Cancer Genetics and Cytogenetics 193:9-18.

(56) References Cited

OTHER PUBLICATIONS

Ye et al., 2009, Pindel: a pattern growth approach to detect break points of large deletions and medium sized insertions from paired-end short reads, Bioinfonrnatics 25(21):2865-71.
Goto, S. A Study on Development of a Deductive Object-Oriented Database and Its Application to Genome Analysis. Diss. PhD Thesis, Kyushu University, 1994.
Parameswaran et al., 2007, A pyrosequencing-tailored nucleotide barcode design unveils opportunities for large-scale sample multiplexing, Nucleic Acids Research 35:e130, Supplementary Material, 18 pages.
Meyer et al., 2008, Parallel tagged sequencing on the 454 platform, Nature Protocols 3(2):267-78.
Margulies, et al., 2005, Genome sequencing in microfabricaled high-density picolilre reactors, Nature 437, Supplemental Material, 52 pages.
Koboldt et al., 2009, VarScan: variant detection in massively parallel sequencing of individual and pooled samples, Bioinformalics 25:2283-85.
International Search Report and Written Opinion for PCT/US2013/044039 mailed Nov. 1, 2013, (15 pages).
Nang et al., 2005, Allele quantification using molecular inversion probes (MIP), Nucleic Acids Research 33{21}:e183.
International Search Report and Written Opinion mailed on Jan. 29, 2015, for Patent Application No. PCT/US2014/060056, filed Oct. 10, 2014, (14 pages).
International Search Report and Written Opinion for PCT/US2013/044039 mailed Nov. 1, 2013, (6 pages).
Browne, Kenneth A., 2002, Journal of American Chemical Society, 124(27)7950-62.
Delcher, AL, et al., Alignment of whole genomes, Nucl. Acids Res., 27:11 (1999).
Husemann, P. and Stoye, J, Phylogenetic Comparative Assembly, Algorithms in Bioinformalics: 9th International Workshop, pp. 145-156, Salzberg, S., and Wamow, T., Eds. Springer-Verlag, Berlin Heidelberg (2009).
Husemann, Phylogentic Comparative Assembly, 2009, 12 pages.
International Search Report and Written Opinion mailed Jun. 10, 2013 for related application PCT/US13/33435 with an International filing dale of Mar. 22, 2013 (7 pages).
Li H. and Durbin R, Fast and accurate short read alignment with Burrows-Wheeler transform, Bioinformatics, 25 (14):1754-60 (2009).
Li, et al., SOAP: short oligonucleolide alignment program, Bioinformatics 24(5):713-14 (2008).
Li, et al., The Sequence Alignment/Map formal and SAMlools, Bioinformatics, 2009, 25(16):2078-9.
Lipman, D.J., Rapid and sensitive protein similarity searches, Science 227(4693):1435-41 (1985).
Margulies, et al., Genome sequencing in microfabricated high-density picolitre reactors, Nature 437:376-380 (2005).
Nicholas, H. B. Jr., et al., Strategies for multiple sequence alignment, Biotechniques 32:572-91 (2002).
Porreca, et al., 2007, Multiplex amplification of large sets of human exons, Nature Methods 4:931-6.
Thorstenson, et al., 1998, An Automated Hydrodynamic Process for Controlled, Unbiased DNA Shearing, Genome Methods 8:848-55.
Cock et al., 2010, The Sanger FASTQ file formal for sequences with quality scores, and the Solexa/Illumina FASTQ variants, Nucleic Acids Res 38(6):1767-1771.
Danecek et al., 2011, The variant call formal and VCFlools, Bioinformalics 27(15):2156-2158.
den Dunnen & Anlonarakis, 2003, Mutation Nomenclature, Curr Prot Hum Genet 7.13.1-7.13.8.
Kumar & Blaxter, 2010, Comparing de novo assemblers for 454 lranscriplome data, Genomics 11 :571.
Li, 2011, Improving SNP discovery by base alignment quality, Bioinformalics 27:1157.
Lin et al., 2008, ZOOM! Zillions Of Oligos Mapped, Bioinformalics 24:2431.

Malewicz, et al., 2010, Pregel: a system for large-scale graph processing, Proceedings ACM SIGMOD Int Conf Management Data 135-146.
Margulies, M. et al., Genome sequencing in micro-fabricated high-density picoliler reactors, Nature, 437:376-380 2005).
McKenna et al., 2010, The Genome Analysis Toolkit: a MapReduce framework for analyzing next-generation DNA sequencing data, Genome Res 20(9):1297-1303.
Rodriguez and Neubauer, 2010, Constructions from Dols and Lines, Bulletin Am Soc Inf Sci Tech 36(6):35-41.
International Search Report and Written Opinion mailed Nov. 16, 2015, for International Application No. PCT/US2015/045247 with International Filing Date Aug. 14, 2015 (10 pages).
International Preliminary Report on Patentability directed to related International Patent Application No. PCT/US2015/045247, issued Feb. 21, 2017; 8 pages.
Robinson et al., 2013, Graph Databases, O'Reilly Media, Inc., Sebastopol, CA (223 pages).
Bunyan, et al., 2004, Dosage analysis of cancer predisposition genes by multiplex ligation-dependent probe amplification, British Journal of Cancer, 91(6):1155-59.
Burrow & Wheeler, 1994, A block-sorting lossless data compression algorithm, Technical Report 124, Digital Equipment Corporation, CA.
Castellani, 2008, Consenses on the use of and interpretation of cystic fibrosis mutation analysis in clinical practice, J Cyst Fib 7:179-196.
Chevreux, B., et al., 1999, Genome Sequence Assembly Using Trace Signals and Additional Sequence Information, Computer Science and Biology: Proceedings of the German Conference on Bioinformatics (GCB) 99:45-56.
Chirgwin, et al., 1979, Isolation of biologically active ribonucleic acid from sources enriched in ribonuclease, Biochemistry, 18:5294-99.
Choe, et al., 2010, Novel CFTR Mutations in a Korean Infant with Cystic Fibrosis and Pancreatic Insufficiency, J Korean Med Sci 25:163-5.
Ciotti, et al., 2004, Triplet Repeat Primed PCR {TP PCR) in Molecular Diagnostic Testing for Friedrich Ataxia, Journal of Molecular Diagnostics 6(4):285-9.
Collins, et al., 2004, Finishing the euchromatic sequence of the human genome, Nature 431.7011:931-45.
Dahl, et al., 2005, Multiplexamplification enabled by selective circularization of large sets of genomic DNA fragments, Nucleic Acids Research 33:e71.
de la Bastide, M. & Mccombie, 2007, W. R, Assembling genome DNA sequences with PHRAP, Current Protocols in Bioinformatics, 17:11.4.1-11.4.15.
Delcher, AL, et al., 1999, Alignment of whole genomes, Nucleic Acids Research, 27:11.
Deng, et al., 2009, Targeted bisulfite sequencing reveals changes in DNA methylation associated with nuclear reprogramming, nature biotechnology 27:353-60 (and supplement).
DiGuistini, S., et al., 2009, De novo genome sequence assembly of a filamentous fungus using Sanger, 454 and llumina sequence data, Genome Biology, 10:R94.
Dong, C. & Yu, B., 2011, Mutation Surveyor: An In Silico Tool for Sequencing Analysis, Methods in Molecular Biology 760:223-37.
Dore, et al., 1969, The Alkaline Denaturation of DNA, Biophysical Journal 9(11):1281-1311.
Dudley, et al., 2009, A Quick Guide for Developing Effective Bioinformatics Programming Skills, PLOS Comput Biol 5 (12):e1000589.
Supplementary European Search Report for EP Application No. 10770071.8 dated Nov. 8, 2012, 17 pages.
Examination Report from the European Patent Office for EP 10770071.8 dated Jul. 16, 2013, 5 pages.
Fares, et al., 2008, Carrier frequency of autosomal-recessive disorders in the Ashkenazi Jewish population: should the rationale for mutation choice for screening be reevaluated?, Prenatal Diagnosis 28:236-41.
Frey, Bruce, 2006, Statistics Hacks 108-115.

(56) References Cited

OTHER PUBLICATIONS

Friedenson, 2005, BRCA1 and BRCA2 Pathways and the Risk of Cancers Other Than Breast or Ovarian, Medscape General Medicine 7(2):60.
Gemayel, et al., 2010, Variable Tandem Repeats Accelerate Evolution of Coding and Regulatory Sequences, Annual Review of Genetics 44:445-77.
Gnirke, et al., 2009, Solution hybrid selection with ultra-long oligonucleolides for massively parallel targeted sequencing, nature biotechnology 27:182-9.
Goto, et al., 2010, BioRuby: bioinformalics software for the Ruby programming language, Bioinformalics 26 (20):2617-9.
Hardenbol, et al., 2003, Multiplexed genotyping with sequence-tagged molecular inversion probes, nature biotechnology 21:673-8.
Harris, et al., 2006, Defects Can Increase the Melting Temperature of DNA-Nanoparticle Assemblies, The Journal of Physical Chemistry B 110:16393-6.
Harris, et al., 2008, Single-Molecule DNA Sequencing of a Viral Genome, Science 320:106-9.
Hodges, et al., 2007, Genome-wide in situ exon capture for selective resequencing, nature genetics 29:1522-7.
Holland, et al., 2008, BioJava: an open-source framework for bioinformatics, Bioinformatics 24(18):2096-97.
Huang, et al., 2008, Comparative analysis of common CFTRpolymorphisms poly-T, TGrepeats and M470V in a health, Chinese population, World J Gastroenterol 14(12):1925-30.
Husemann, P. & Stoye, 2009, Phylogenetic Comparative Assembly, Algorithms in Bioinformatics: 9th International Workshop, pp. 145-156, Salzberg, S., and Warnow, T., Eds. Springer-Verlag, Berlin Heidelberg.
International Preliminary Report on Palentability for PCT/US2010/01293, dated Oct. 28, 2010.
International Search Report and Written Opinion mailed Apr. 3, 2012, for International Patent Application No. PCT/US2011/065098, filed Dec. 15, 2011 (8 pages).
International Search Report and Written Opinion mailed Aug. 12, 2013, for International Patent Application No. PCT/US13/36575, filed Apr. 15, 2013 (9 pages).
International Search Report and Written Opinion mailed Feb. 25, 2013 for International Patent Application No. PCT/US12/55362.
International Search Report and Written Opinion mailed Jun. 10, 2013, for International Patent Application No. PCT/US13/33435, filed Mar. 22, 2013 (6 pages).
International Search Report and Written Opinion mailed Jun. 14, 2012, for International Patent Application No. PCT/US12/29790, filed Mar. 20, 2012 (8 pages).
International Search Report and Written Opinion mailed Nov. 1, 2013, for International Patent Application No. PCT/US2013/044039, filed Jun. 4, 2013 (6 pages).
International Search Report and Written Opinion mailed on Feb. 4, 2014, for Patent Application No. PCT/US13/62842, filed Oct. 1, 2013 (5 pages).
International Search Report and Written Opinion mailed on Oct. 28, 2010, for Patent Application No. PCT/US2010/001293, filed Apr. 30, 2010 (8 pages).
Iqbal, et al., 2012, De novo assembly and genotyping of variants using colored de Bruijn graphs, Nature Genetics, 44 (2):226-233.
Jaijo, et al., 2010, Microarray-Based Mutation Analysis of 183 Spanish Families with Usher Syndrome, Investigative Ophthalmology & Visual Science 51(3):1311-7.
Jones, et al., 2008, Core Signaling Pathways in Human Pancreatic Cancers Revealed by Global Genomic Analyses, Science 321(5897):1801-1806.
Kent, W.J., 2002, BLAT-The BLAST-like alignment tool, Genome Research 4: 656-664.
Kircher, et al., 2010, High-throughput DNA sequencing—concepts and limitations, Bioassays 32:524-36.
Krawitz, 2010, Microindel detection in short-read sequence data, Bioinformatics 26(6):722-729.
Kreindler, 2010, Cystic fibrosis: exploiting its genetic basis in the hunt for new therapies, Pharmacol Ther 125 (2):219-229.
Kumar, S., et al., 2010, Comparing de novo assemblers for 454 transcriptome data, Genomics 11:571.
Kurtz, S., et al., 2004, Versatile and open software for comparing large genomes, Genome Biology, 5:R12.
Schwartz, Stuart, 2011, Clinical Utility of Single Nucleotide Polymorphism Arrays, Clinics in Laboratory Medicine 31 (4):581-94.
Sequeira, et al., 1997, Implementing generic, object—0riented models in biology, Ecological Modeling 94.1:17-31.
Sievers F., et al., 2011, Fast, scalable generation of high-quality protein multiple sequence alignments using Clustal Omega, Mol Syst Biol 7:539.
Simpson, JT, et al., 2009, ABySS: A parallel assembler for short read sequence data, Genome Res., 19(6): 1117-23.
Slater, G., & Birney, E, 2005, Automated generation of heuristics for biological sequence comparison, BMC Bioinformatics 6:31.
Soni, G. V., & Meller, A, 2007, Progress toward ultrafast DNA sequencing using solid-state nanopores, Clin Chem 53: 1996-2001.
Spanu, PD., et al., 2010, Genome expansion and gene loss in powdery mildew fungi reveal tradeoffs in extreme parasitism, Science 330(6010): 1543-46.
Summerer, Daniel, 2009, Enabling technologies of genomic-scale sequence enrichment for targeted high-throughput sequencing, Genomics 94:363-8.
Thauvin-Robinet, et al., 2009, The very low penetrance of cystic fibrosis for the R117H mutation: a reappraisal for genetic counseling and newborn screening, J Med Genet 46:752-758.
Thompson, et al., 1994, Clustal W: improving the sensitivity of progressive multiple sequence alignment through sequence weighting, position-specific gap penalities and matrix choice, Nucl. Acids. Res., 22:4673-80.
Thorvaldsdottir, et al., 2012, Integrative Genomics Viewer (IGV): high-performance genomics data visualization and exploration, Briefings in Bioinformatics 24(2): 178-92.
Tokino, 1996, Characterization of the human p57 KIP2 gene: alternative splicing, insertion/deletion polymorphisms in VNTR sequences in the coding region, and mutational analysis, Human Genetics 96:625-31.
Turner, et al., 2009, Methods for Genomic Partitioning, Annual Review of Genomics and Human Genetics 10:263-84.
Warner, et al., 1996, A general method for the detection of large CAG repeat expansions by fluorescent PCR, Journal Medical Genetics 33(12):1022-6.
Warren, R, et al., 2007, Assembling millions of short DNA sequences using SSAKE, Bioinformatics, 23:500-501.
Watson et al., 2004, Cystic fibrosis population carrier screening: 2004 revision of American College of Medical Genetics mutation panel, Genetics in Medicine 6(5):387-391.
Wittung, et al., 1997, Extended DNA-Recognition Repertoire of Peptide Nucleic Acid (PNA): PNA-dsDNA Triplex Formed with Cytosine-Rich Homopyrimidine PNA, Biochemistry 36:7973.
Yau, et al., 1996, Accurate diagnosis of carriers of deletions and duplications in Duchenne/Becker muscular dystrophy by fluorescent dosage analysis, Journal Medical Genetics 33(7):550-8.
Yoo, et al., 2009, Applications of DNA Microarray in Disease Diagnostics, Journal of Microbiology and Biotechnology 19(7):635-46.
Yoshida, et al., 2004, Role of BRCA1 and BRCA2 as regulators of DNA repair, transcription, and cell cycle in response to DNA damage, Cancer Science 95(11) 866-71.
Yu, 2007, A novel set of DNA methylation markers in urine sediments for sensitive/specific detection of bladder cancer Clin Cancer Res 13(24):7296-7304.
Zerbino D.R. et al., 2008, Velvet: algorithms for de novo short read assembly using de Bruijn graphs, Genome Research 18 (5):821-829.
Zhang, et al., 2011, Is Mitochondrial tRNAphe Variant m.593T.Ca Synergistically Pathogenic Mutation in Chinese LHON Families with m.11778G.A? PLOS ONE 6(10):e26511.
Zhao F., et al., 2009, PGA4genomics for comparative genome assembly based on genetic algorithm optimization, Genomics. 94(4):284-6.

(56) References Cited

OTHER PUBLICATIONS

Zheng, et al., 2011, iAssembler: a package for de novo assembly of Roche-454/Sanger transcriptome sequences, BMC Bioinformatics 12:453.
Zimmerman, et al., 2010, A novel custom resequencing array for dilated cardiomyopathy, Genetics in Medicine 12 (5):268-78.
Thompson, et al., 2011, The properties and applications of single-molecule DNA sequencing, Genome Biology 12 (2):217, 10 pages.
Australian Patent Examination Report No. 1 issued Aug. 12, 2014, for Australian Patent Application No. J010242073, filed Apr. 30, 2010, 4 pages.
Supplementary European Search Report issued Aug. 26, 2014, for European Patent Application No. 12765217.0, filed Mar. 20, 2012, 5 pages.
Bickle, Thomas A & Kruger, Detlev, H., 1993, Biology of DNA Restriction, Microbiological Reviews 57(2):434-50.
S. Gustincich et al., Bio Techniques, 1991, 11: 298-302.
Williams, 2003, Restriction Endonucleases Classification, Properties, and Applications, Molecular Biotechnology 23 (3):225-43.
Wallace, et al., 1979, Hybridization of synthetic oligodeoxyribonucteotides to dp x 17 4DNA:the effect of single base pair mismatch, Nucleic Acids Research 6:3543-3557.
Alazard, et al., 2005, Sequencing Oligonucleotides by Enrichment of Coupling Failures Using Matrix-Assisted Laser Desorption/Ionization Time-of-Flight Mass Spectrometry, Current Protocols in Nucleic Acid Chemistry 10.10.1-10.10.7.
International Search Report and Written Opinion mailed on Sep. 3, 2014 for International Patent Application No. PCT/US14/27324, filed Mar. 14, 2014 (8 pages).
Fitch, 1970, "Distinguishing homologs from analogous proteins," Syst Biol 19(2):99-113.
Jensen, 2001, "Orthologs and paralogs—we need to get it right," Genome Biol 2(8):1002-1002.3.
Danecek, 2011, "The variant call format and VCFtools," Bioinformatics 27(15):2156-58.
Malewicz, 2010, "Pregel: a system for large-scale graph processing," Proc. ACM SIGMOD Int Conf Mgmt Data 135-46.
McKenna, 2010, "The Genome Analysis Toolkit: a MapReduce framework for analyzing next-generation DNA sequencing data," Genome Res 20(9):1297-1303.
Rodriguez, 2010, "Constructions from Dots and Lines," Bull Am Soc Inf Sci Tech 36(6):35-41, available at http://arxiv.org/pdf/1006.2361.pdf.
Kneen, 1998, "Green fluorescent protein as a noninvasive intracellular pH indicator," Biophys J 74(3):1591-99.
Llopis, 1998, "Measurement of cytosolic, mitochondrial, and Golgi pH in single living cells with green fluorescent proteins," Proc Natl Acad Sci USA 95(12):6803-08.
Brownstein, 2014, "An international effort towards developing standards for best practices in analysis, interpretation and reporting of clinical genome sequencing results in the CLARITY Challenge," Genome Biol 15:R53.
Hallam, 2014, "Validation for clinical use of, and initial clinical experience with, a novel approach to population-based carrier screening using high-throughput, next-generation DNA sequencing," J Mol Diagn 16:180-89.
MacArthur, 2014, "Guidelines for investigating causality of sequence variaants in human disease," Nature 508:469-76.
Maddalena, 2005, "Technical standards and guidelines: molecular genetic testing for ultra-rare disorders," Genet Med 7:571-83.
Richards, 2008, "ACMG recommendations for standards for interpretation and reporting of sequence variations: Revisions 2007," Genet Med 10:294-300.
Strom, 2005, "Mutation detection, interpretation, and applications in the clinical laboratory setting," Mutal Res 573:160-67.
Umbarger, 2014, "Next-generation carrier screening," Genet Med 16:132-40.
MacDonald et al. The Database of Genomic Variants: a curated collection of structural variation in the human genome Nucleic Acids Research vol. 42, pp. D986-D992 (Year: 2014).
Shendure et al. Next-generation DNA sequencing Nature Biotechnology vol. 26, pp. 1135-1145 (Year: 2008).
Huang et al. IEEE 2013 3rd International Conference on Consumer Electronics, Communications and Networks pp. 533-536 (Year: 2013).
Wikipedia Graph Database page [retrieved on Mar. 7, 2019] Retrieved from the Internet https://en.wikipedia.org/wikiGraph_database.

* cited by examiner

```
##fileformat=VCFv4.1
##fileDate=20110413
##source=VCFtools
##reference=file:///refs/human_NCBI36.fasta
##contig=<ID=1,length=249250621,md5=1b22b98cdeb4a9304cb5d48026a85128,species="Homo Sapiens">
##contig=<ID=X,length=155270560,md5=7e0e2e580297b7764e31dbc80c2540dd,species="Homo Sapiens">
##INFO=<ID=AA,Number=1,Type=String,Description="Ancestral Allele">
##INFO=<ID=H2,Number=0,Type=Flag,Description="HapMap2 membership">
##FORMAT=<ID=GT,Number=1,Type=String,Description="Genotype">
##FORMAT=<ID=GQ,Number=1,Type=Integer,Description="Genotype Quality">
##FORMAT=<ID=DP,Number=1,Type=Integer,Description="Read Depth">
##ALT=<ID=DEL,Description="Deletion">
##INFO=<ID=SVTYPE,Number=1,Type=String,Description="Type of structural variant">
##INFO=<ID=END,Number=1,Type=Integer,Description="End position of the variant">
#CHROM POS  ID    REF  ALT    QUAL FILTER INFO                FORMAT   SAMPLE1   SAMPLE2
1      1    .     ACG  A,AT   40   PASS   .                   GT:DP    1/1:13    2/2:29
1      2    .     C    T,CT   .    PASS   H2;AA=T             GT       0|1       2/2
1      5    rs12  A    G      67   PASS   .                   GT:DP    1|0:16    2/2:20
X      100  .     T    <DEL>  .    PASS   SVTYPE=DEL;END=299  GT:GQ:DP 1:12:.    0/0:20:36
```

FIG. 2

SYSTEMS AND METHODS FOR GENETIC ANALYSIS

CROSS-REFERENCE TO RELATED APPLICATION

This application is a continuation application of U.S. application Ser. No. 14/826,595, filed: Aug. 14, 2015, which claims the benefit of and priority to U.S. Provisional Application No. 62/037,861, filed Aug. 15, 2014, the entire contents of each of which are incorporated herein by reference in their entirety.

TECHNICAL FIELD

The invention relates to medical genetics.

BACKGROUND

Before having children, a person may turn to genetic screening to find out if he or she is a carrier of a genetic condition. Genetic carrier screening can be done using next-generation sequencing (NGS), which produces millions of "base-calls" read from the person's genome. Typically, those base calls are then compared to a reference genome to determine their clinical significance. While all 3.2 billion base-pairs of the human genome are available for use as a reference (e.g., as hg18), knowing the clinical significance of features in the person's genome requires turning to medical literature or specialized databases of mutations. For example, the Online Mendelian Inheritance in Man (OMIM) database contains information on genetic disorders in over 12,000 human genes.

The volumes of data that must be stored, compared, and understood are a significant obstacle to realizing the full potential of NGS as a carrier screening tool. Generally, the time required for analysis and reporting is proportional to the amount of data in the databases. The structure of those databases requires exhaustive index table lookups for each comparison. Also, since databases designs must be locked in prior to use, a clinician's use of the data system is limited to what the database designer foresaw as the likely qualities of the data. A clinician who discovers a new phenomenon—such as and a novel combination of mutations associated with an unexpected disease—may be faced with a data system that does not even provide a means for entering or describing this information.

SUMMARY

The invention provides systems and methods for genetic analysis in which entities such as mutations, patients, samples, alleles, and clinical information are individually represented and stored as nodes and in which relationships between entities are also individually represented and stored. Each node and relationship can be stored using a fixed-size record and nodes can be flexibly invoked to represent any novel entity without disrupting the information already represented in the system. By forsaking the traditional database schema of indexed tables, the run time for queries need not be proportional to the amount of data in the tables. Instead, queries that start with a certain node can find the relevant related nodes in time proportional only to the number of nodes in the results that match the query. Moreover, novel entities and relationships can be inserted into the data system upon discovery with no disruption to the data or operation of the system. Thus, novel mutations can be added or related to disease phenotypes or appropriate literature references as that new information is discovered and observed. The time required for a query of—for example—relationships between a patient and disease-associated alleles in that patient's genome will be proportional to the number of results that are found for inclusion in a report for that patient. Where sequencing uncovers novel mutations or genotype/phenotype associations, those entities and relationships can be brought into the system and included in the reporting without requiring any changes or re-design to the underlying system architecture. In methods and systems of the invention, NGS results, patient information, and medical information can be stored in a graph database and analyzed using graph processing approaches and languages. This provides for very rapid querying and report generation, independent of the size of the underlying data store.

Since report generation is rapid and not linked to the underlying volume of data, and since systems of the invention may easily accommodate the volumes of data associated with NGS sequencing and human genome based analyses, systems and methods of the invention may be employed for NGS-based carrier screening and provide meaningful results to patients.

Additionally, the invention includes the insight that the clinical significance of mutations—or "variants", e.g., as documented in NGS results such as Variant Call Format (VCF) files—can be shown by relating the mutation to a particular allele of a gene and showing where in the literature the variant is reported as pathogenic or benign while connecting this information back to a patient and lab sample for reporting purposes. Sequencing by existing NGS technologies may provide abundant high-quality raw data in the form of sequence files such as FASTA, FASTQ, Sequence Alignment Map (SAM), Binary Alignment Map (BAM), or VCF files. Systems and methods of the invention can be used to extract relevant data from those files into the described nodes to support the rapid querying and report generation useful for NGS carrier screening. For example, systems of the invention may include an Application Programming Interface (API) that takes as input VCF files and creates a network of nodes representing patients, samples, VCF files, VCF records, variants, alleles, and literature reports with relationships connecting adjacent pairs of those nodes according to their natural relationships. The system supports a genomics analysis clinical pipeline even as it changes and can accommodate the loading in of external data. The system can be implemented using a graph database and related software. Systems of the invention support a variety of analyses and use cases. For example, with NGS-based carrier screening implemented using the described graph database structure for analysis and reporting, it becomes easy to query and report such phenomenon as allele frequencies.

Importantly, systems and methods of the invention support the curation of variants. Curating variants includes identifying an individual variant in sequencing results, researching medical literature for information about the variant, classifying the variant (e.g., pathogenic, benign, somewhere in between), and accessioning that information into the database for use in subsequent reports on patient samples in which that variant is implicated. Using the nodes and relationships provided by the invention, variants can be connected to alleles, literature references, medical information, or combinations thereof. If changes are subsequently made (e.g., a missense mutation is re-classified as a nonsense mutation), other features of the system infrastructure are not disrupted. Thus the active curation of variants is accommodate and improves the system.

In certain aspects, the invention provides a method for analyzing mutations. The method includes obtaining data representing a mutation in a genome of an individual and using a node in a graph database to store a description of the mutation. The node has stored within it a pointer to an adjacent node that provides information about a clinical significance of the variant. The method includes querying the graph database to provide a report of the clinical significance of the mutation in the genome of the individual.

The data representing the mutation may be obtained by obtaining a sample that includes a nucleic acid from the individual and sequencing the nucleic acid to obtain a sequence read file that includes the data. The sample may be represented in the graph database using a sample node and the sample node may be connected via a pointer to a read file node representing the sequence read file. The graph database may include nodes representing people, nodes representing genomic variants relative to a reference, and nodes representing literature reports on medical relevance of the genomic variants as well as edges defining relationships between pairs of the nodes.

In some embodiments, the data representing a mutation is obtained as part of a file such as a variant call file (VCF), a sequence alignment map (SAM) file, a binary alignment map (BAM) file, a FASTA file, or a FASTQ file. The file may be represented in the graph database (e.g., using a file node) and a pointer to the file node may be stored in the mutation node.

In certain embodiments, the data representing a mutation comprises a description of the mutation as a variant of a reference human genome. The description of the mutation may be provided as a VCF record in a VCF file. The method may include obtaining sequencing data that represents a plurality of mutations in the genome of the individual—each of the plurality of mutations being represented as variant calls relative to a human genome reference. For each of the plurality of mutations, a corresponding variant node in the graph database is used to store a description of that mutation.

Aspects of the invention provide a system for describing genetic information. The system includes at least one computer comprising memory coupled to a processor. The system has at least a portion of a graph database stored therein. The system is operable to obtain data representing a mutation in a genome of an individual, use a variant node in the graph database to store a description of the mutation, and store—within the variant node—a pointer to an adjacent node that provides information about a clinical significance of the mutation. The system may be used to query the graph database to provide a report of the clinical significance of the mutation in the genome of the individual. As discussed above, the data representing a mutation may be obtained as part of a file such as a VCF file. The system may represent the file as a file node in the graph database and store, in the variant node, a pointer to the file node.

The data representing the mutation may be provided as a sequence read file that includes that data. In certain embodiments, the system is operable use the graph database to represent a biological sample from the individual with a sample node and connect the sample node via a pointer to a read file node representing the sequence read file.

The system may be operated to obtain sequencing data representing a plurality of mutations in the genome of the individual (e.g., as variant calls relative to a human genome reference) and use, for each of the plurality of mutations, a corresponding variant node in the graph database to store a description of that mutation. The system links the individual to an allele node based on the plurality of mutations.

In a preferred aspect, the invention provides: a system for describing genetic information, the system comprising: at least one computer comprising memory coupled to a processor, the system having at least a portion of a graph database stored therein, wherein the system is operable to: obtain data representing a mutation in a genome of an individual; use a node in the graph database to store a description of the mutation; store, in the node, a pointer to an adjacent node that provides information about a clinical significance of the mutation; and query the graph database to provide a report of the clinical significance of the mutation in the genome of the individual. Preferably a pointer identifies a physical location in the memory at which the adjacent node is stored. Thus each node may be stored at a specific physical location the memory. Each such specific physical location is referenced by a pointer (which itself optionally may be stored within a node at a physical location that is referenced, in-turn, by another pointer). Preferably, each pointer identifies a physical location in the memory subsystem at which the adjacent object is stored. In the preferred embodiments, the pointer or native pointer is manipulatable as a memory address in that it points to a physical location on the memory but also dereferencing the pointer accesses intended data. That is, a pointer is a reference to a datum stored somewhere in memory; to obtain that datum is to dereference the pointer. The feature that separates pointers from other kinds of reference is that a pointer's value is interpreted as a memory address, at a low-level or hardware level. The speed and efficiency of the described low-level, or hardware level, memory referencing allows for incredibly rapid graph traversals, which means that data content can scale up unbounded but reporting actionable medical genetic information will not require amounts of time that scale up with the data content. Use of hardware level references, or index-free adjacency, uncouples the time requirements for medical genetics reporting from data content volume.

In a first embodiment of the preferred aspect, the system is operable to obtain the data representing the mutation by receiving at least one sequence read file that includes the data. Preferably the system of the first embodiment is further operable to represent, in the graph database, a biological sample from the individual using a sample node and connect the sample node via a pointer to a read file node representing the sequence read file.

In a second embodiment of the preferred aspect, the data representing the mutation is obtained as part of a file. In the second embodiment, the file may have a format selected from the group consisting of variant call format; sequence alignment map; binary alignment map; FASTA; and FASTQ. Preferably in the second embodiment the system is operable to represent the file as a file node in the graph database and store, in the variant node, a pointer to the file node. Optionally, the system is further operable to represent, in the graph database, a biological sample from the individual using a sample node and connect the sample node via a pointer to a read file node representing the sequence read file.

In a third embodiment of the preferred aspect, the data representing the mutation comprises a description of the mutation as a variant of a reference human genome. In the third embodiment, the description of the mutation may optionally be obtained from a VCF record in a VCF file. Additionally, the system of the third embodiment may be further operable to represent, in the graph database, a biological sample from the individual using a sample node and connect the sample node via a pointer to a read file node representing the sequence read file.

In a fourth embodiment of the preferred aspect, the system is further operable to: obtain sequencing data representing a plurality of mutations in the genome of the individual, the plurality of mutations being represented as variant calls relative to a human genome reference; use, for each of the plurality of mutations, a corresponding variant node in the graph database to store a description of that mutation; and link the individual to an allele node based on the plurality of mutations. In the fourth embodiment, the graph database may include: nodes representing people, nodes representing genomic variants relative to a reference, and nodes representing literature reports on medical relevance of the genomic variants; and edges defining relationships between pairs of the nodes. The system of the fourth embodiment may be further operable to represent, in the graph database, a biological sample from the individual using a sample node and connect the sample node via a pointer to a read file node representing the sequence read file.

In a fifth embodiment of the preferred aspect, the graph database comprises: nodes representing people, nodes representing genomic variants relative to a reference, and nodes representing literature reports on medical relevance of the genomic variants; and edges defining relationships between pairs of the nodes. In the fifth embodiment, the system may be further operable to represent, in the graph database, a biological sample from the individual using a sample node and connect the sample node via a pointer to a read file node representing the sequence read file.

BRIEF DESCRIPTION OF THE DRAWINGS

FIG. 2 gives a sample of an exemplary VCF file.

DETAILED DESCRIPTION

The invention relates to using a graph database in genetic analyses to link mutation data to extrinsic data. Entities such as mutations, patients, samples, alleles, and clinical information are individually represented and stored as nodes and relationships between entities are also individually represented and stored. Each node and relationship can be stored using a fixed-size record and nodes can be flexibly invoked to represent any entity without disrupting the existing data. Systems and methods of the invention may be used for obtaining data representing a mutation in an individual and using a variant node in a graph database to store a description of the mutation. The variant node has stored within it a pointer to an adjacent node that provides information about a clinical significance of the variant. The graph database can be queried to provide a report of the clinical significance of the mutation. In certain embodiments, systems and methods of the invention operate within the context of a carrier screening workflow and provide a querying and reporting tool for carrier screening.

Figure 1:
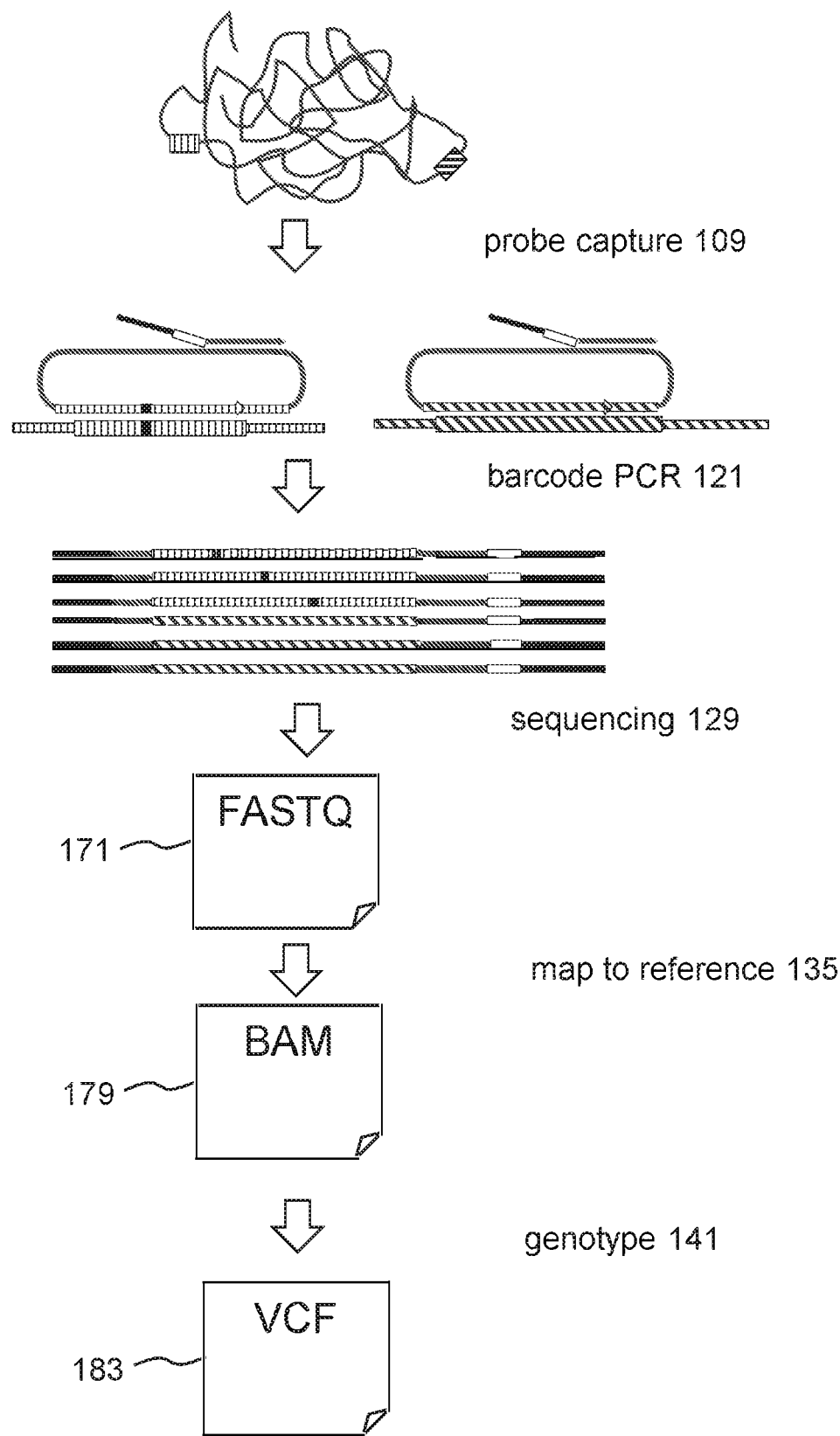
FIG. 1 illustrates an exemplary NGS workflow for carrier screening.

FIG. 1 illustrates an exemplary NGS workflow for carrier screening. The workflow combines automated, optimized molecular inversion probe target capture 109 with molecular barcoding to maximize the sample throughput of an NGS machine and employs assembly and alignment methods that allow accurate identification of both substitution and insertion/deletion lesions. The workflow is applicable to, for example, genes in which loss-of-function mutations cause recessive Mendelian disorders often included as part of routine carrier screening. A screening or analysis may begin with obtaining nucleic acid from a sample.

Nucleic acid in a sample can be any nucleic acid, including for example, genomic DNA in a tissue sample, cDNA amplified from a particular target in a laboratory sample, or mixed DNA from multiple organisms. In some embodiments, the sample includes homozygous DNA from a haploid or diploid organism. For example, a sample can include genomic DNA from a patient who is homozygous for a rare recessive allele. In other embodiments, the sample includes heterozygous genetic material from a diploid or polyploidy organism with a somatic mutation such that two related nucleic acids are present in allele frequencies other than 50 or 100%, i.e., 20%, 5%, 1%, 0.1%, or any other allele frequency.

In one embodiment, nucleic acid template molecules (e.g., DNA or RNA) are isolated from a biological sample containing a variety of other components, such as proteins, lipids, and non-template nucleic acids. Nucleic acid template molecules can be obtained from any cellular material, obtained from animal, plant, bacterium, fungus, or any other cellular organism. Biological samples for use in the present invention also include viral particles or preparations. Nucleic acid template molecules can be obtained directly from an organism or from a biological sample obtained from an organism, e.g., from blood, urine, cerebrospinal fluid, seminal fluid, saliva, sputum, stool, and tissue. Any tissue or body fluid specimen (e.g., a human tissue of bodily fluid specimen) may be used as a source for nucleic acid to use in the invention. Nucleic acid template molecules can also be isolated from cultured cells, such as a primary cell culture or cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin, e.g. amplified/isolated DNA from the freezer.

Generally, nucleic acid can be extracted, isolated, amplified, or analyzed by a variety of techniques such as those described by Green and Sambrook, Molecular Cloning: A Laboratory Manual (Fourth Edition), Cold Spring Harbor Laboratory Press, Woodbury, NY 2,028 pages (2012); or as described in U.S. Pat. Nos. 7,957,913; 7,776,616; 5,234,809; U.S. Pub. 2010/0285578; and U.S. Pub. 2002/0190663.

Nucleic acid from a sample may optionally be fragmented or sheared to a desired length, using a variety of mechanical, chemical, and/or enzymatic methods. DNA may be randomly sheared via sonication using, for example, an ultra-sonicator sold by Covaris (Woburn, MA), brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid is fragmented by sonication. In another embodiment, nucleic acid is fragmented by a hydroshear instrument. Generally, individual nucleic acid template molecules can be from about 2 kb bases to about 40 kb. In a particular embodiment, nucleic acids are about 6 kb-10 kb fragments. Nucleic acid molecules may be single-stranded, double-stranded, or double stranded with single-stranded regions (for example, stem- and loop-structures).

A biological sample may be lysed, homogenized, or fractionated in the presence of a detergent or surfactant as needed. Suitable detergents may include an ionic detergent (e.g., sodium dodecyl sulfate or N-lauroylsarcosine) or a nonionic detergent (such as the polysorbate 80 sold under the trademark TWEEN by Uniqema Americas (Paterson, NJ) or $C_{14}H_{22}O(C_2H_4)n$, known as TRITON X-100).

In certain embodiments, genomic DNA samples are input to a molecular inversion probe capture 109 reaction. Molecular inversion probes may be designed to capture the coding regions and as well as well-characterized noncoding regions of genes. Such probes may include 5' and 3' targeting arms (extension and ligation, respectively) of, for example, about a total of 40 nucleotides and being designed to flank 130-bp target regions. Each target is captured 109 by multiple probes that anneal to non-overlapping genomic intervals. PCR is performed 121 using primers containing patient-specific barcodes, yielding barcode libraries. Genomic DNA may be subjected to multiplex target capture using molecular inversion probes. Captured product may be subjected to PCR to attach molecular barcodes in a manner that allow sequencing from either end of the captured region.

PCR may be used as described or any other amplification reaction may be performed. Amplification refers to production of additional copies of a nucleic acid sequence and is generally carried out using polymerase chain reaction (PCR) or other technologies known in the art. The amplification reaction may be any amplification reaction known in the art that amplifies nucleic acid molecules such as PCR (e.g., nested PCR, PCR-single strand conformation polymorphism, ligase chain reaction, strand displacement amplification and restriction fragments length polymorphism, transcription based amplification system, rolling circle amplification, and hyper-branched rolling circle amplification, quantitative PCR, quantitative fluorescent PCR (QF-PCR), multiplex fluorescent PCR (MF-PCR), real time PCR (RTPCR), restriction fragment length polymorphism PCR). See U.S. Pat. Nos. 5,242,794; 5,494,810; 4,988,617; 6,582,938; 4,683,195; and 4,683,202, hereby incorporated by reference. Primers for PCR, sequencing, and other methods can be prepared by cloning, direct chemical synthesis, and other methods known in the art. Primers can also be obtained from commercial sources such as Eurofins MWG Operon (Huntsville, AL) or Life Technologies (Carlsbad, CA).

Amplification adapters may be attached to the fragmented nucleic acid. Adapters may be commercially obtained, such as from Integrated DNA Technologies (Coralville, IA). In certain embodiments, the adapter sequences are attached to the template nucleic acid molecule with an enzyme. The enzyme may be a ligase or a polymerase. The ligase may be any enzyme capable of ligating an oligonucleotide (RNA or DNA) to the template nucleic acid molecule. Suitable ligases include T4 DNA ligase and T4 RNA ligase, available commercially from New England Biolabs (Ipswich, MA). Methods for using ligases are well known in the art. The polymerase may be any enzyme capable of adding nucleotides to the 3' and the 5' terminus of template nucleic acid molecules.

Embodiments of the invention involve attaching the bar code sequences to the template nucleic acids e.g., for barcode PCR 121. In certain embodiments, a bar code is attached to each fragment. In other embodiments, a plurality of bar codes, e.g., two bar codes, are attached to each fragment. A bar code sequence generally includes certain features that make the sequence useful in sequencing reactions. For example the bar code sequences are designed to have minimal or no homo-polymer regions, i.e., 2 or more of the same base in a row such as AA or CCC, within the bar code sequence. The bar code sequences are also designed so that they are at least one edit distance away from the base addition order when performing base-by-base sequencing, ensuring that the first and last base do not match the expected bases of the sequence.

The bar code sequences are designed such that each sequence is correlated to a particular portion of nucleic acid, allowing sequence reads to be correlated back to the portion from which they came. Methods of designing sets of bar code sequences are shown for example in U.S. Pat. No. 6,235,475, the contents of which are incorporated by reference herein in their entirety. In certain embodiments, the bar code sequences range from about 5 nucleotides to about 15 nucleotides. In a particular embodiment, the bar code sequences range from about 4 nucleotides to about 7 nucleotides. Since the bar code sequence is sequenced along with the template nucleic acid, the oligonucleotide length should be of minimal length so as to permit the longest read from the template nucleic acid attached. Generally, the bar code sequences are spaced from the template nucleic acid molecule by at least one base (minimizes homo-polymeric combinations). In certain embodiments, the bar code sequences are attached to the template nucleic acid molecule, e.g., with an enzyme. The enzyme may be a ligase or a polymerase, as discussed below. Attaching bar code sequences to nucleic acid templates is shown in U.S. Pub. 2008/0081330 and U.S. Pub. 2011/0301042, the contents of which are incorporated by reference herein in its entirety. Methods for designing sets of bar code sequences and other methods for attaching bar code sequences are shown in U.S. Pat. Nos. 7,544,473; 7,537,897; 7,393,665; 6,352,828; 6,172,218; 6,172,214; 6,150,516; 6,138,077; 5,863,722; 5,846,719; 5,695,934; and 5,604,097, each incorporated by reference.

After any processing steps (e.g., obtaining, isolating, fragmenting, amplification, or barcoding), nucleic acid can be sequenced 129.

Sequencing 129 may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used includes, for example, use of sequencing-by-synthesis systems sold under the trademarks GS JUNIOR, GS FLX+ and 454 SEQUENCING by 454 Life Sciences, a Roche company (Branford, CT), and described by Margulies, M. et al., Genome sequencing in micro-fabricated high-density picotiter reactors, Nature, 437:376-380 (2005); U.S. Pat. Nos. 5,583,024; 5,674,713; and 5,700,673, the contents of which are incorporated by reference herein in their entirety. 454 sequencing involves two steps. In the first step of those systems, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used is SOLiD technology by Applied Biosystems from Life Technologies Corporation (Carlsbad, CA). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is removed and the process is then repeated.

Another example of a DNA sequencing technique that can be used is ion semiconductor sequencing using, for example, a system sold under the trademark ION TORRENT by Ion Torrent by Life Technologies (South San Francisco, CA). Ion semiconductor sequencing is described, for example, in Rothberg, et al., An integrated semiconductor device enabling non-optical genome sequencing, Nature 475:348-352 (2011); U.S. Pub. 2010/0304982; U.S. Pub. 2010/0301398; U.S. Pub. 2010/0300895; U.S. Pub. 2010/0300559; and U.S. Pub. 2009/0026082, the contents of each of which are incorporated by reference in their entirety.

Another example of a sequencing 129 technology that can be used is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which are incorporated by reference in their entirety.

Another example of a sequencing technology that can be used includes the single molecule, real-time (SMRT) technology of Pacific Biosciences (Menlo Park, CA). In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used is nanopore sequencing (Soni & Meller, 2007, Progress toward ultrafast DNA sequence using solid-state nanopores, Clin Chem 53(11):1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used involves using a chemical-sensitive field effect transistor (chemFET) array to sequence DNA (for example, as described in U.S. Pub. 2009/0026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using an electron microscope as described, for example, by Moudrianakis, E. N. and Beer M., in Base sequence determination in nucleic acids with the electron microscope, III. Chemistry and microscopy of guanine-labeled DNA, PNAS 53:564-71 (1965). In one example of the technique, individual DNA molecules are labeled using metallic labels that are distinguishable using an electron microscope. These molecules are then stretched on a flat surface and imaged using an electron microscope to measure sequences.

Sequencing according to embodiments of the invention generates a plurality of reads. Reads according to the invention generally include sequences of nucleotide data less than about 5000 bases in length, or less than about 150 bases in length. In certain embodiments, reads are between about 80 and about 90 bases, e.g., about 85 bases in length. In some embodiments, methods of the invention are applied to very short reads, i.e., less than about 50 or about 30 bases in length. Sequence read data can include the sequence data as well as meta information. Sequence read data can be stored in any suitable file format including, for example, VCF files, FASTA files or FASTQ files, as are known to those of skill in the art. In some embodiments, PCR product is pooled and sequenced (e.g., on an Illumina HiSeq 2000). Raw .bcl files are converted to qseq files using bclConverter (Illumina). FASTQ files are generated by "de-barcoding" genomic reads using the associated barcode reads; reads for which barcodes yield no exact match to an expected barcode, or contain one or more low-quality base calls, may be discarded. Reads may be stored in any suitable format such as, for example, FASTA or FASTQ format.

FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. The word following the ">" symbol is the identifier of the sequence, and the rest of the line is the description (both are optional). There should be no space between the ">" and the first letter of the identifier. It is recommended that all lines of text be shorter than 80 characters. The sequence ends if another line starting with a ">" appears; this indicates the start of another sequence.

The FASTQ format is a text-based format for storing both a biological sequence (usually nucleotide sequence) and its corresponding quality scores. It is similar to the FASTA format but with quality scores following the sequence data. Both the sequence letter and quality score are encoded with a single ASCII character for brevity. The FASTQ format is a de facto standard for storing the output of high throughput sequencing instruments such as the Illumina Genome Analyzer. Cock et al., 2009, The Sanger FASTQ file format for sequences with quality scores, and the Solexa/Illumina FASTQ variants, Nucleic Acids Res 38(6):1767-1771.

For FASTA and FASTQ files, meta information includes the description line and not the lines of sequence data. In some embodiments, for FASTQ files, the meta information includes the quality scores. For FASTA and FASTQ files, the sequence data begins after the description line and is present typically using some subset of IUPAC ambiguity codes optionally with "-". In a preferred embodiment, the sequence data will use the A, T, C, G, and N characters, optionally including "-" or U as-needed (e.g., to represent gaps or uracil).

Following sequencing, reads are preferably mapped 135 to a reference using assembly and alignment techniques known in the art or developed for use in the workflow. Various strategies for the alignment and assembly of sequence reads, including the assembly of sequence reads into contigs, are described in detail in U.S. Pat. No. 8,209,130, incorporated herein by reference. Strategies may include (i) assembling reads into contigs and aligning the contigs to a reference; (ii) aligning individual reads to the reference; (iii) assembling reads into contigs, aligning the contigs to a reference, and aligning the individual reads to the contigs; or (iv) other strategies known to be developed or known in the art. Mapping 135, it can be seen, may employ assembly steps, alignment steps, or both. Assembly can be implemented, for example, by the program 'The Short Sequence Assembly by k-mer search and 3' read Extension' (SSAKE), from Canada's Michael Smith Genome Sciences Centre (Vancouver, B.C., CA) (see, e.g., Warren et al., 2007, Assembling millions of short DNA sequences using SSAKE, Bioinformatics, 23:500-501). SSAKE cycles through a table of reads and searches a prefix tree for the longest possible overlap between any two sequences. SSAKE clusters reads into contigs.

Another read assembly program is Forge Genome Assembler, written by Darren Platt and Dirk Evers and available through the SourceForge web site maintained by Geeknet (Fairfax, VA) (see, e.g., DiGuistini et al., 2009, De novo sequence assembly of a filamentous fungus using Sanger, 454 and Illumina sequence data, Genome Biology, 10:R94). Forge distributes its computational and memory consumption to multiple nodes, if available, and has therefore the potential to assemble large sets of reads. Forge was written in C++ using the parallel MPI library. Forge can handle mixtures of reads, e.g., Sanger, 454, and Illumina reads.

Assembly through multiple sequence alignment can be performed, for example, by the program Clustal Omega, (Sievers et al., 2011, Fast, scalable generation of high-quality protein multiple sequence alignments using Clustal Omega, Mol Syst Biol 7:539), ClustalW, or ClustalX (Larkin et al., 2007, Clustal W and Clustal X version 2.0, Bioinformatics, 23(21):2947-2948) available from University College Dublin (Dublin, Ireland).

Another exemplary read assembly program known in the art is Velvet, available through the web site of the European Bioinformatics Institute (Hinxton, UK) (Zerbino & Birney, Velvet: Algorithms for de novo short read assembly using de Bruijn graphs, Genome Research 18(5):821-829). Velvet implements an approach based on de Bruijn graphs, uses information from read pairs, and implements various error correction steps.

Read assembly can be performed with the programs from the package SOAP, available through the website of Beijing Genomics Institute (Beijing, CN) or BGI Americas Corporation (Cambridge, MA). For example, the SOAPdenovo program implements a de Bruijn graph approach. SOAP3/GPU aligns short reads to a reference sequence.

Another read assembly program is ABySS, from Canada's Michael Smith Genome Sciences Centre (Vancouver, B.C., CA) (Simpson et al., 2009, ABySS: A parallel assembler for short read sequence data, Genome Res., 19(6):1117-23). ABySS uses the de Bruijn graph approach and runs in a parallel environment.

Read assembly can also be done by Roche's GS De Novo Assembler, known as gsAssembler or Newbler (NEW assemBLER), which is designed to assemble reads from the Roche 454 sequencer (described, e.g., in Kumar & Blaxter, 2010, Comparing de novo assemblers for 454 transcriptome data, Genomics 11:571 and Margulies 2005). Newbler accepts 454 Flx Standard reads and 454 Titanium reads as well as single and paired-end reads and optionally Sanger reads. Newbler is run on Linux, in either 32 bit or 64 bit versions. Newbler can be accessed via a command-line or a Java-based GUI interface. Additional discussion of read assembly may be found in Li et al., 2009, The Sequence alignment/map (SAM) format and SAMtools, Bioinformatics 25:2078; Lin et al., 2008, ZOOM! Zillions Of Oligos Mapped, Bioinformatics 24:2431; Li & Durbin, 2009, Fast and accurate short read alignment with Burrows-Wheeler Transform, Bioinformatics 25:1754; and Li, 2011, Improving SNP discovery by base alignment quality, Bioinformatics 27:1157. Assembled sequence reads may preferably be aligned to a reference.

Methods for alignment and known in the art and may make use of a computer program that performs alignment, such as Burrows-Wheeler Aligner.

In certain embodiments, reads are aligned to hg18 on a per-sample basis using Burrows-Wheeler Aligner version 0.5.7 for short alignments, and genotype calls are made using Genome Analysis Toolkit. See McKenna et al., 2010, The Genome Analysis Toolkit: a MapReduce framework for analyzing next-generation DNA sequencing data, Genome Res 20(9):1297-1303. High-confidence genotype calls may be defined as having depth ≥50 and strand bias score ≤0. Clinical significance of variant calls is an important question in carrier screening and will be addressed below. Other computer programs for assembling reads are known in the art. Such assembly programs can run on a single general-purpose computer, on a cluster or network of computers, or on specialized computing devices dedicated to sequence analysis.

In some embodiments, de-barcoded fastq files are obtained as described above and partitioned by capture region (exon) using the target arm sequence as a unique key. Reads are assembled in parallel by exon using SSAKE version 3.7 with parameters "-m 30 -o 15". The resulting contiguous sequences (contigs) can be aligned to hg18 (e.g., using BWA version 0.5.7 for long alignments with parameter "-r 1"). In some embodiments, short-read alignment is performed as described above, except that sample contigs (rather than hg18) are used as the input reference sequence. Software may be developed in Java to accurately transfer coordinate and variant data (gaps) from local sample space to global reference space for every BAM-formatted alignment. Genotyping and base-quality recalibration may be performed on the coordinate-translated BAM files using the GATK program.

In some embodiments, any or all of the steps of the invention are automated. For example, a Perl script or shell script can be written to invoke any of the various programs discussed above (see, e.g., Tisdall, Mastering Perl for Bioinformatics, O'Reilly & Associates, Inc., Sebastopol, CA 2003; Michael, R., Mastering Unix Shell Scripting, Wiley Publishing, Inc., Indianapolis, Indiana 2003). Alternatively, methods of the invention may be embodied wholly or partially in one or more dedicated programs, for example, each optionally written in a compiled language such as C++ then compiled and distributed as a binary. Methods of the invention may be implemented wholly or in part as modules within, or by invoking functionality within, existing sequence analysis platforms. In certain embodiments, methods of the invention include a number of steps that are all invoked automatically responsive to a single starting queue (e.g., one or a combination of triggering events sourced from human activity, another computer program, or a machine). Thus, the invention provides methods in which any or the steps or any combination of the steps can occur automatically responsive to a queue. Automatically generally means without intervening human input, influence, or interaction (i.e., responsive only to original or pre-queue human activity).

Mapping 135 sequence reads to a reference, by whatever strategy, may produce output such as a text file or an XML file containing sequence data such as a sequence of the nucleic acid aligned to a sequence of the reference genome. In certain embodiments (e.g., see FIG. 1) mapping 135 reads to a reference produces results stored in SAM or BAM file 179 and such results may contain coordinates or a string describing one or more mutations in the subject nucleic acid relative to the reference genome. Alignment strings known in the art include Simple UnGapped Alignment Report (SUGAR), Verbose Useful Labeled Gapped Alignment Report (VULGAR), and Compact Idiosyncratic Gapped Alignment Report (CIGAR) (Ning, Z., et al., Genome Research 11(10):1725-9 (2001)). These strings are implemented, for example, in the Exonerate sequence alignment software from the European Bioinformatics Institute (Hinxton, UK).

In some embodiments, a sequence alignment is produced—such as, for example, a sequence alignment map (SAM) or binary alignment map (BAM) file—comprising a CIGAR string (the SAM format is described, e.g., in Li, et al., The Sequence Alignment/Map format and SAMtools, Bioinformatics, 2009, 25(16):2078-9). In some embodiments, CIGAR displays or includes gapped alignments one-per-line. CIGAR is a compressed pairwise alignment format reported as a CIGAR string. A CIGAR string is useful for representing long (e.g. genomic) pairwise alignments. A CIGAR string is used in SAM format to represent alignments of reads to a reference genome sequence.

A CIGAR string follows an established motif. Each character is preceded by a number, giving the base counts of the event. Characters used can include M, I, D, N, and S (M=match; I=insertion; D=deletion; N=gap; S=substitution). The CIGAR string defines the sequence of matches/mismatches and deletions (or gaps). For example, the CIGAR string 2MD3M2D2M will mean that the alignment contains 2 matches, 1 deletion (number 1 is omitted in order to save some space), 3 matches, 2 deletions and 2 matches. In general, for carrier screening or other assays such as the NGS workflow depicted in FIG. 1, sequencing results will be used in genotyping 141.

Output from mapping 135 may be stored in a SAM or BAM file 179, in a variant call format (VCF) file 183, or other format. In an illustrative embodiment, output is stored in a VCF file, although methods described herein are applicable to other file formats such as SAM or BAM files, as will be readily apparent to one of skill in the art.

FIG. 2 gives a sample of an exemplary VCF file 183. A typical VCF file 183 will include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described in Danecek et al., 2011, The variant call format and VCFtools, Bioinformatics 27(15):2156-2158.

The data contained in a VCF file 183 as shown for example in FIG. 2 represents the variants, or mutations, that are found in the nucleic acid that was obtained from the sample from the patient and sequenced. In its original sense, mutation refers to a change in genetic information and has come to refer to the present genotype that results from a mutation. As is known in the art, mutations include different types of mutations such as substitutions, insertions or deletions (INDELs), translocations, inversions, chromosomal abnormalities, and others. By convention in some contexts where two or more versions of genetic information or alleles are known, the one thought to have the predominant frequency in the population is denoted the wild type and the other(s) are referred to as mutation(s). In general in some contexts an absolute allele frequency is not determined (i.e., not every human on the planet is genotyped) but allele frequency refers to a calculated probable allele frequency based on sampling and known statistical methods and often an allele frequency is reported in terms of a certain population such as humans of a certain ethnicity. Variant can be taken to be roughly synonymous to mutation but referring to a genotype being described in comparison or with reference to a reference genotype or genome. For example as used in bioinformatics variant describes a genotype feature in comparison to a reference such as the human genome (e.g., hg18 or hg19 which may be taken as a wild type). An NGS workflow and genotype 141 generates data representing one or more mutations in a genome of an individual that are generally reported as variants, or "variant calls", in, for example, a VCF file 183.

With continuing reference to FIG. 2, a VCF file 183 includes data representing one or more mutations. Those data may be analyzed by methods of the invention to provide a report of the clinical significance of the mutations in the genome of the individual.

Figure 3:
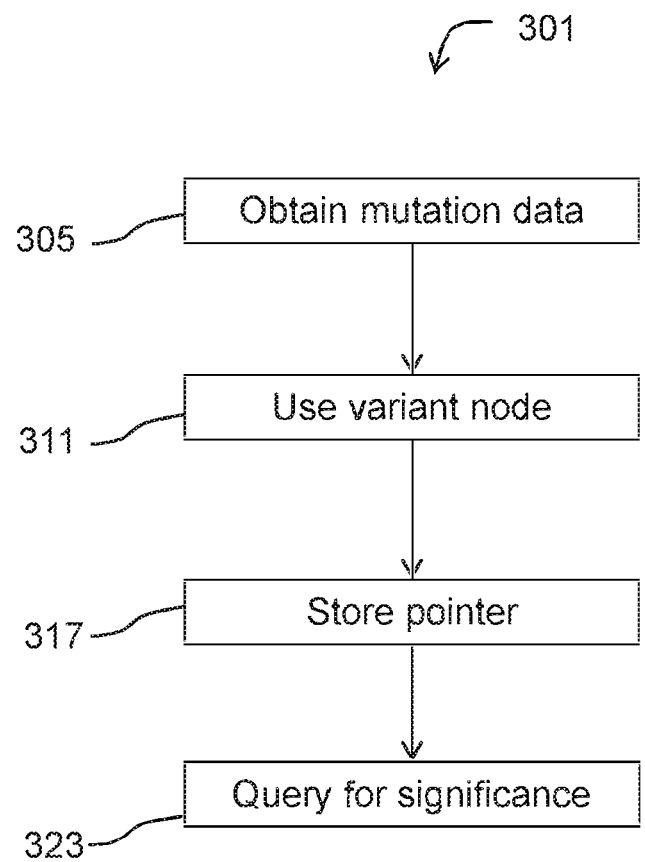
FIG. 3 diagrams a method for analyzing mutations.

FIG. 3 diagrams a method 301 for analyzing mutations according to the invention. One benefit of a method 301 is an ability to provide information about the clinical significance of mutations in a patient's genome from data such as that provided by sequencing, e.g., in FASTA/FASTQ files, SAM/BAM files, or VCF files. Methods include obtaining 305 data representing a mutation in a genome of an individual by, for example, the sampling, sequencing, and mapping methods described above. A variant node in a graph database is used 311 to store a description of the mutation. A pointer is stored 317 in the variant node and the pointer points to an adjacent node that provides information about a clinical significance of the variant. Method 301 includes querying 323 the graph database to obtain information reporting the clinical significance of the mutation in the genome of the individual.

To illustrate operation of the invention, the following discusses obtaining mutation data in a VCF file, although one of skill in the art will readily see that the discussion is extensible to other formats. Using a workflow such as the NGS workflow illustrated in FIG. 1, a VCF file containing mutation data is obtained 305. The VCF file may be parsed to isolate its component pieces of information and to consider each piece of information for its own significance. There exist programs or application programming interfaces (APIs) for parsing VCF files 183 or a program may be written that parses data from the VCF file.

Figure 4:
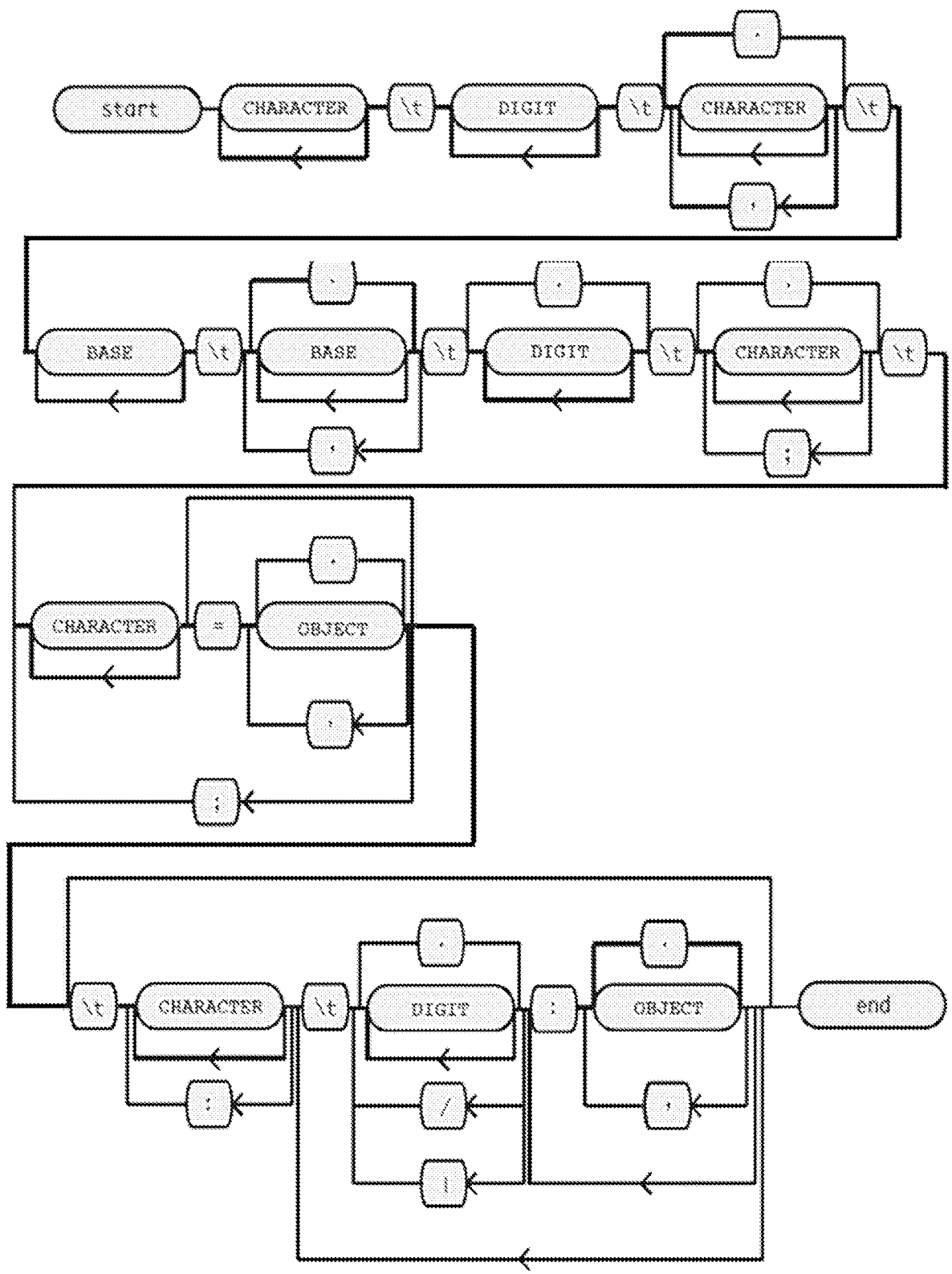
FIG. 4 gives a flow chart for a VCF file parser.

FIG. 4 gives a flow chart for a VCF parser. The flow chart shown in FIG. 4 represents the conceptual steps that may go into parsing a VCF file and extracting component information. Since the various action blocks and loops are defined according to the format of the VCF file as standardized (e.g., in Danecek, 2011, Bioinformatics 27:2156), each character of information that is extracted is treated for what it is. Thus, using VCF file 183 from FIG. 2 for reference, the "A" that appears on line 16, character 7 (counting 1 tab as 1 character) is treated as a nucleotide in the reference and the "A" that appears in line 17, character 17 is simply part of the word "PASS" in the FILTER column. It is further recognized that line 16 (and any subsequent line) is a single VCF record within a VCF file. Each record from the VCF file represents something found by sequencing the nucleic acid from the sample from the patient. Each patient, having numerous genes in their genome, has numerous alleles. Thus where carrier screening is performed for a patient, the VCF run (e.g., all the VCF files produced by the NGS sequencing) ultimately documents and shows the various alleles in the patient's genome that were probed for by the probes used.

Figure 5:
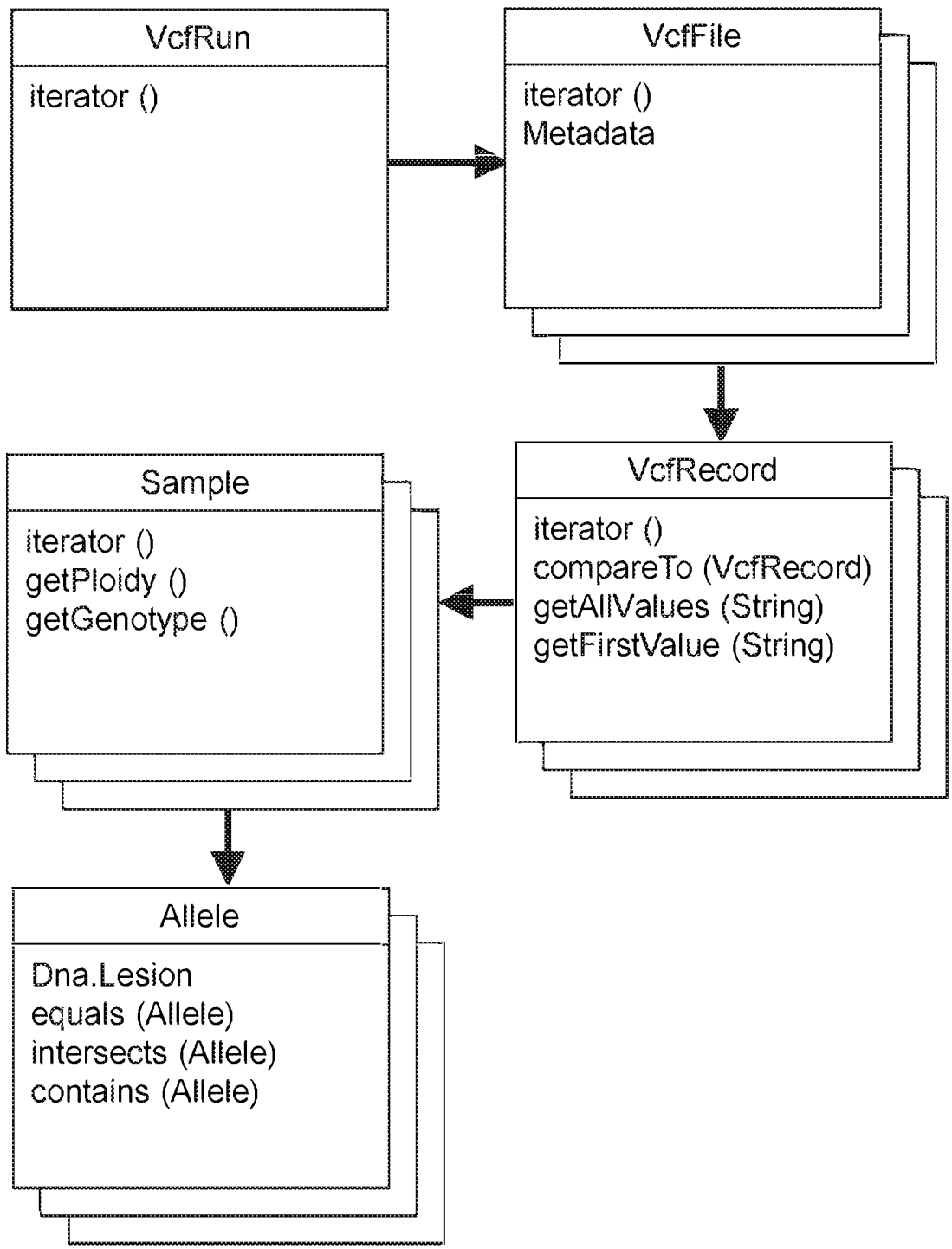
FIG. 5 presents a model of data received from parsing a VCF file.

FIG. 5 presents a model of data received from parsing a VCF. As just discussed, one run from the sequencing instruments can produce a plurality of VCF files. Each VCF file typically contains a plurality of VCF records. Those records ultimately relate back to the samples from which they were derived, and the samples can each contain a plurality of alleles. However, this relationship just described can also be described using an entity relationship diagram, or ERD.

Figure 6:
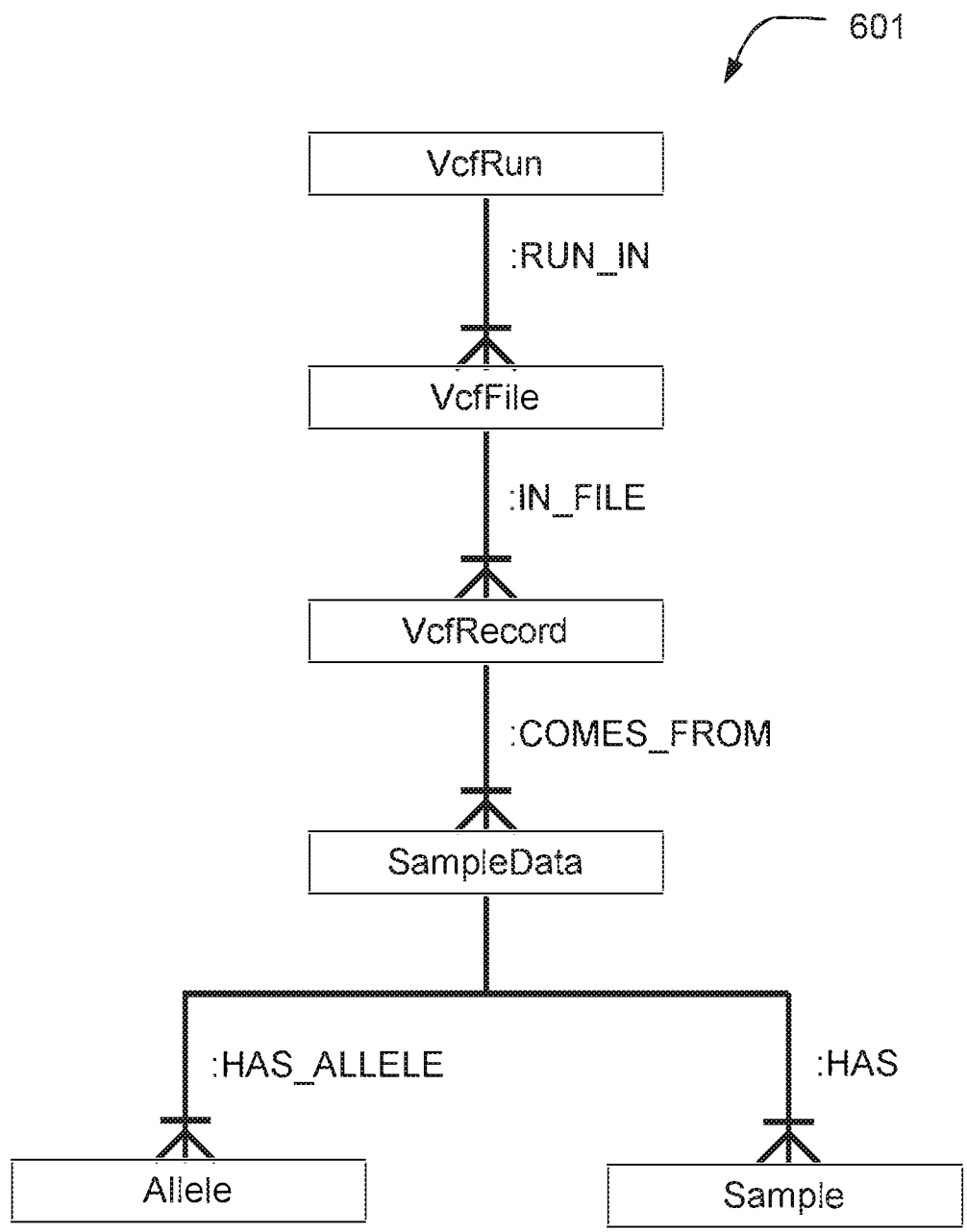
FIG. 6 shows an entity relationship diagram (ERD) of the data modeled by FIG. 5.

FIG. 6 shows an entity relationship diagram (ERD) 601 of the data modeled by FIG. 5. An insight of the invention is that the ERD 601 satisfies the definition of a graph as used in graph theory within mathematics and computer science. Graph theory provides a well-known mathematical tool for representing systems. Graph theory is the mathematical study of properties of formal mathematical structures called graphs. In that context, a graph is a finite set of points, termed vertices or nodes, connected by links termed edges or arcs. A graph thus generally defines a set of vertices and a set of pairs of vertices, which are the edges of the graph. There are several types of graphs in graph theory. The type of a particular graph largely depends upon the features of its components, namely the attributes of its vertices and edges. For example, when the set of pairs includes only distinct elements, the graph is called a simple graph; when one or more pairs are connected by multiple edges the graph is called a multi-graph; when one or more vertices are connected to themselves the graph is called a pseudo-graph; when the edges are assigned with directions the graph is called a directed graph or a digraph; and when the pairs of vertices are unordered the graph is called undirected. Additional illustrative background on graph theory may be found in U.S. Pat. No. 8,463,895 to Arora; U.S. Pat. No. 8,462,161 to Barber; U.S. Pat. No. 7,523,117 to Zhang; U.S. Pat. No. 6,360,235 to Tilt; U.S. Pub. 2013/0222388 to McDonald; and U.S. Pub. 2007/0244675 to Shai, the contents of each of which are incorporated by reference.

It can be observed that ERD 601 presents a graph—a collection of vertices and edges—or another description would be a set of nodes and the relationships that connect them. Graphs represent entities as nodes and the ways in which those entities relate to the world as relationships. This general-purpose, expressive structure allows graphs to model all kinds of phenomena such as NGS sequence files and their relationships to the source biological samples and genetic concepts like certain alleles. There are various dominant graph data models such as the property graph, Resource Description Framework (RDF) triples, and hypergraphs. In certain embodiments, a graph database used in the invention uses the property graph model.

A property graph has characteristics such as containing nodes and relationships (which are illustrated by ERD 601 in FIG. 6). The nodes contain properties (key-value pairs). Relationships are named and directed, and have a start and end node; and relationships can also contain properties. A graph database management system (henceforth, a graph database) is an online database management system with Create, Read, Update, and Delete (CRUD) methods that expose a graph data model. Graph databases according to the invention may be described or characterized according to the underlying storage, the processing engine, or both.

Regarding the underlying storage, some graph databases use native graph storage that is optimized and designed for storing and managing graphs. Some databases serialize the graph data into a relational database, an object-oriented database, or some other general-purpose data store and present graph database functionality on top of that.

Regarding the processing engine, some graph databases use index-free adjacency, meaning that connected nodes physically "point" to each other in the database. More broadly, graph databases can include any database that from the user's perspective behaves like a graph database (i.e., exposes a graph data model through CRUD operations) qualifies as a graph database. In certain embodiments, however, the invention provides the significant performance advantages of index-free adjacency. Native graph processing may describe graph databases that use index-free adjacency.

A benefit of native graph storage is that it is engineered for performance and scalability. A benefit of non-native graph storage is that it typically depends on a mature non-graph backend (such as MySQL) whose production characteristics are well understood by operations teams. Native graph processing (index-free adjacency) benefits traversal performance.

In the graph data model, relationships are included as entities that themselves are stored as objects. (Whereas other database management systems require connections between entities to be inferred using contrived properties such as foreign keys, or out-of-band processing like map-reduce.) By assembling the simple abstractions of nodes and relationships into connected structures, graph databases provide arbitrarily sophisticated models that map closely to the problem domain (e.g., FIG. 5). The resulting models are simpler and at the same time more expressive than those produced using traditional relational databases and the other NOSQL stores.

Any suitable graph database can be used to implement the systems and methods described herein. Exemplary graph databases may include Microsoft Infinite Graph, Titan, OrientDB, Neo4j, *dex, Franz Inc., AllegroGraph, and Hypergraphdb. Preferably, systems and methods of the invention employ a graph compute engine.

A graph compute engine is a technology that enables global graph computational algorithms to be run against large datasets. Graph compute engines are designed to do things like identify clusters in the data, or answer questions about how entities are connected, and particularly to trace across a series of linked ideas (e.g., SNP to allele to genetic condition to a literature reference providing a clinical significance of the allele containing the SNP).

A variety of different types of graph compute engines exist. Most notably there are in-memory/single machine graph compute engines like Cassovary, and distributed graph compute engines like Pegasus or Giraph. A distributed graph compute engine may be structured as described in Malewicz, et al., 2010, Pregel: a system for large-scale graph processing, Proceedings ACM SIGMOD Int Conf Management Data 135-146. Also see Rodriguez and Neubauer, 2010, Constructions from Dots and Lines, Bulletin Am Soc Inf Sci Tech 36(6):35-41.

In preferred embodiments, systems and methods of the invention store mutation descriptions using a graph database and analyze mutations in graph space.

To achieve the benefits potentially offered by using a graph database, a genetic analysis pipeline and methodology according to the invention uses nodes as well as named and directed relationships, with both the nodes and relationships serving as containers for properties. With continuing reference to FIG. 6, nodes and relationships are illustrated and index-free adjacency is discussed.

A database engine that utilizes index-free adjacency is one in which each node maintains direct references to its adjacent nodes. Each node thus acts as a micro-index of other nearby nodes, which is much cheaper than using global indexes. It means that query times are independent of the total size of the graph, and are instead simply proportional to the amount of the graph searched.

A non-native graph database engine, in contrast, uses (global) indexes to link nodes together. These indexes add a layer of indirection to each traversal, thereby incurring greater computational cost. Proponents for native graph processing argue that index-free adjacency is crucial for fast, efficient graph traversals. To understand why native graph processing is so much more efficient than graphs based on heavy indexing, consider the following. Depending on the implementation, index lookups could be $O(\log n)$ in algorithmic complexity versus $O(1)$ for looking up immediate relationships. To traverse a network of m steps, the cost of the indexed approach, at $O(m \log n)$, dwarfs the cost of $O(m)$ for an implementation that uses index-free adjacency.

Index-free adjacency provides lower-cost "joins." With index-free adjacency, bidirectional joins are effectively pre-computed and stored in the database as relationships. In contrast, when using indexes to fake connections between records, there is no actual relationship stored in the database. This becomes problematic for traversals in the "opposite" direction from the one for which the index was constructed. Because such traversals require a brute-force search through the index—which is an $O(n)$ operation—and joins like this are simply too costly to be of any practical use. Index free adjacency provides surprising benefits in the context of reporting clinical significance of the results of NGS-based carrier screening in that the concepts involved are of just such a nature as to naturally lend themselves to representation using the pre-computed bidirectional joins offered by index free adjacency.

For at least these reasons, systems and methods of certain embodiments of the invention use index-free adjacency to ensure high-performance traversals. FIG. 6 shows how relationships eliminate the need for index lookups. A graph database can use relationships, not indexes, for fast traversals A general-purpose graph database relationships can be traversed in either direction (tail to head, or head to tail) extremely cheaply. Starting from a given VcfRun or a given allele, a graph processing engine can find the related other one of those two at a very low computation cost.

In certain embodiments, systems and methods of the invention use native graph storage. If index-free adjacency is the key to high-performance traversals, queries, and writes, then one key aspect of the design of a graph database is the way in which graphs are stored. An efficient, native graph storage format supports extremely rapid traversals for arbitrary graph algorithms an important reason for using graphs.

A graph database such as Neo4j stores graph data in a number of different store files. Each store file may contain the data for a specific part of the graph (e.g., nodes, relationships, properties). The division of storage responsibilities—particularly the separation of graph structure from property data—facilitates performant graph traversals, even though it means the user's view of their graph and the actual records on disk are structurally dissimilar. FIGS. 7-10 illustrates a node and relationship storage structure as implemented by a graph database of the invention.

Figure 7:
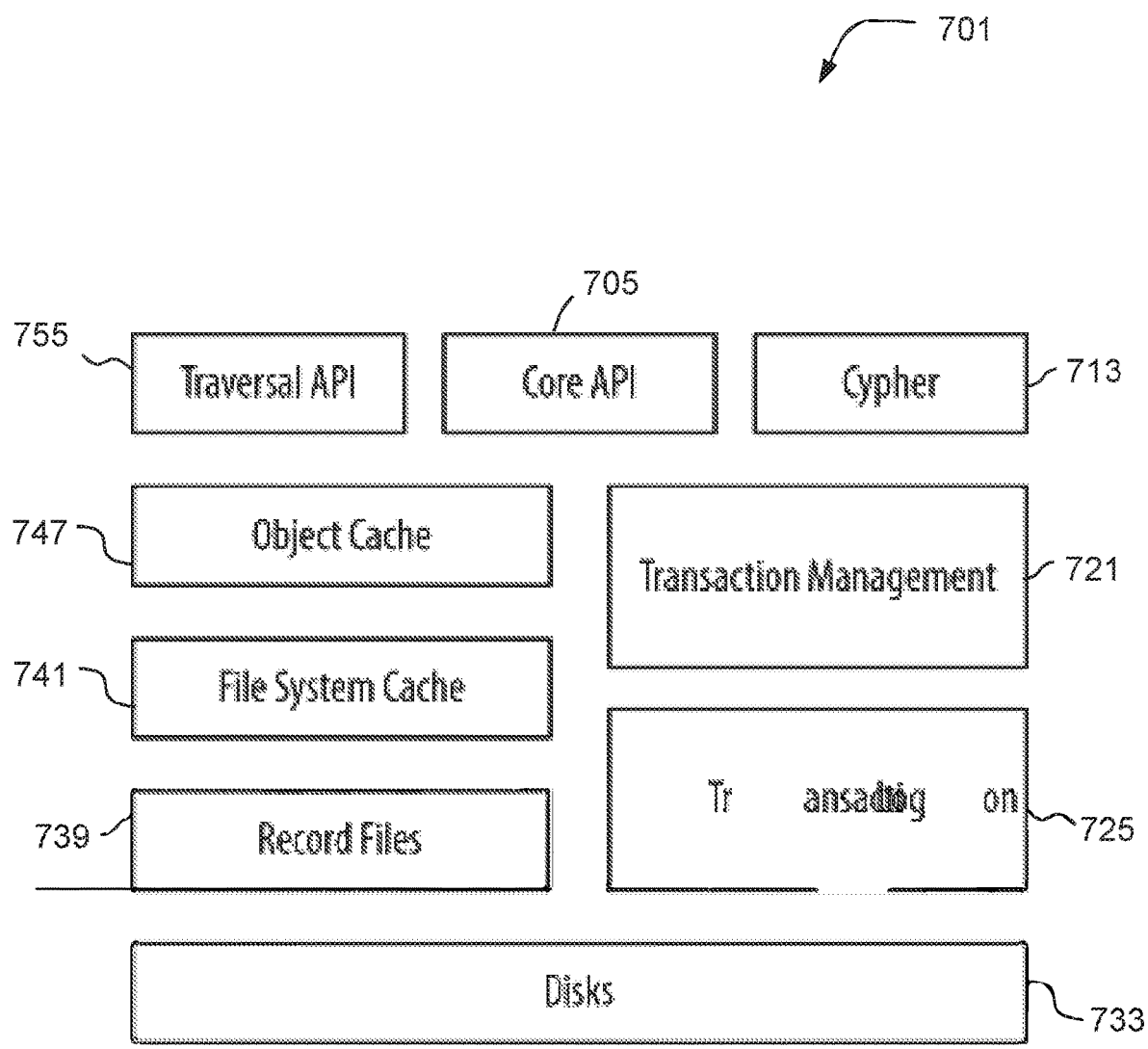
FIG. 7 diagrams a high-level architecture of a system of the invention.

FIG. 7 diagrams a high-level architecture 701 of systems of certain embodiments of the invention. From the bottom-up, systems may operate using files on disk 733. Record files 739 provide a basic level of storage to support the file system cache 741. The object cache 747 is kept at a high level for rapid access as discussed herein. Additionally, the disks 733 can store a transaction log 725, which is written to by a transaction management module 721. A graph database such as Neo4j includes or provides a traversal API 755, core API 705, and a query language 713 such as Cypher.

Figure 8:
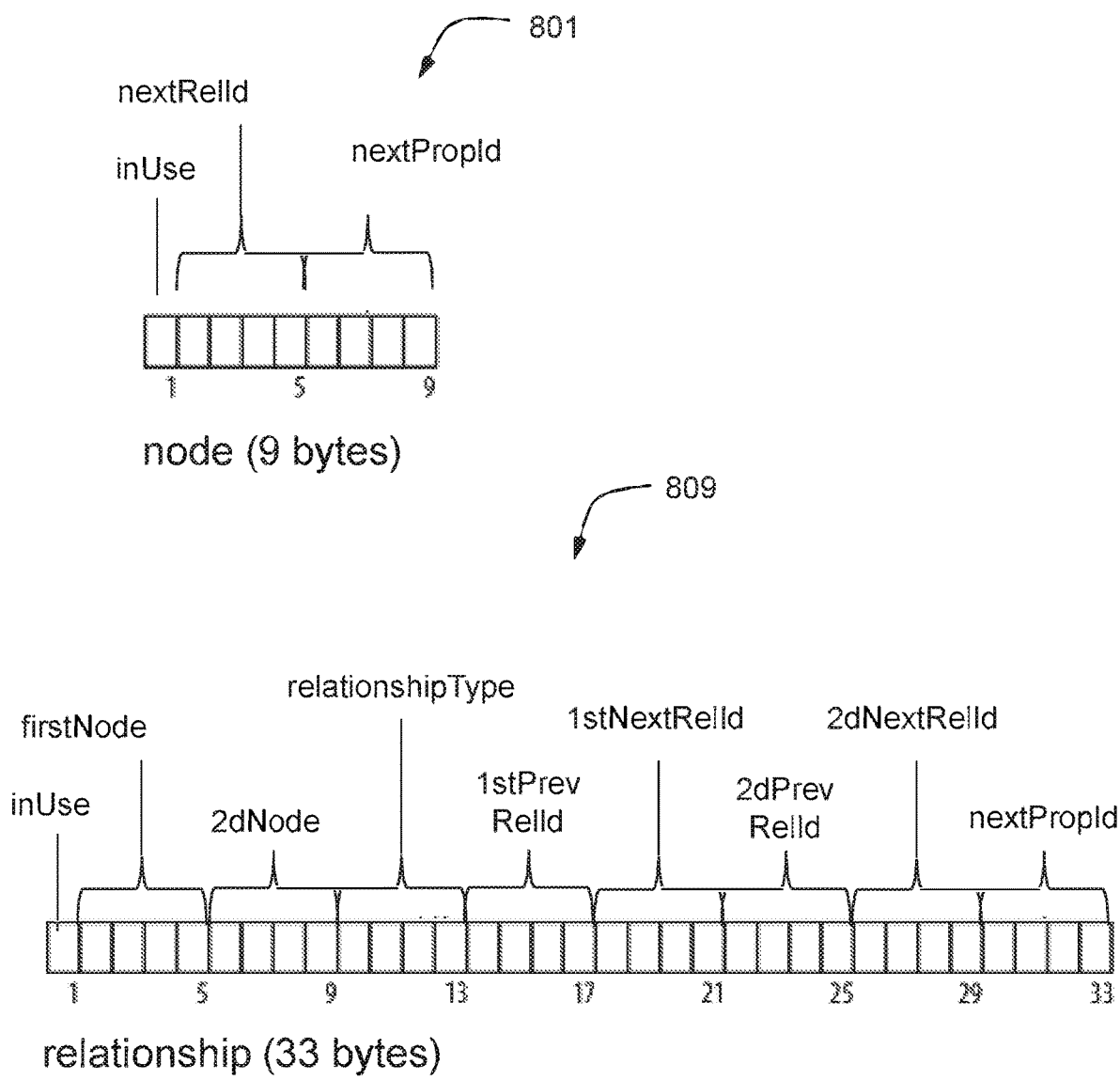
FIG. 8 illustrates a structure for nodes and relationships on disk.

FIG. 8 illustrates the structure of nodes 801 and relationships 809 on disk as may be deployed within a physical structure of systems of the invention. The node store file stores node records. Every node created in the user-level graph ends up in the node store. Preferably, the node store is a fixed-size record store. While the precise values or traits may be varied as necessary or best-suited to the invention, in the illustrated embodiment, each node record 801 is nine bytes in length. Fixed-size records enable fast lookups for nodes in the store file. To illustrate, if a node has id 100, then it can be known that its record begins 900 bytes into the file. Based on this format, the database can directly compute a record's location, at cost O(1), rather than performing a search, which would be cost O(log n). It is noted that fixed-size record stores provide an improvement to a computer in the sense that information storage efficiently exploits the physical storage device for very fast retrieval and very fast look-ups. Thus, genetic queries according to methods and systems of the invention actually proceed faster at a hardware level than prior art approaches—the computer itself is sped up by the implementations described.

The first byte of a node 801 record is the in-use flag. This tells the database whether the record is currently being used to store a node. The next four bytes represent the ID of the first relationship connected to the node, and the last four bytes represent the ID of the first property for the node. The node record is lightweight and contains just pointers to lists of relationships and properties.

Correspondingly, relationships are stored in a relationship store file Like the node store, the relationship store consists of fixed-sized records—in this case each relationship record 809 is 33 bytes long. Each relationship record 809 contains the IDs of the nodes at the start and end of the relationship, a pointer to the relationship type (which is stored in the relationship type store), and pointers for the next and previous relationship records for each of the start and end nodes. These last pointers are part of what is often called the relationship chain.

The node and relationship stores are concerned only with the structure of the graph, not its property data. Both stores use fixed-sized records so that any individual record's location within a store file can be rapidly computed given its ID. The significance can hardly be overstated: the described structure improves the operation of the hardware itself.

Using the described structures, given the way that the various store files are stored on disk, graph processing operations are low-cost. Each of the node records contains a pointer to that node's first property and first relationship in a relationship chain. To read a node's properties, one may follow the singly linked list structure beginning with the pointer to the first property. To find a relationship for a node, one may follow that node's relationship pointer to its first relationship and then follow the doubly linked list of relationships for that particular node (that is, either the start node doubly linked list, or the end node doubly linked list) until the relationship of interest is found.

Having found the record for the relationship of interest, that relationship's properties can be read (if there are any) using the same singly linked list structure as is used for node properties, or the node records can be examined for the two nodes the relationship connects using its start node and end node IDs. These IDs, multiplied by the node record size, give the immediate offset of each node in the node store file.

In some embodiments, systems and methods of the invention use doubly-linked lists in the relationship store. It is noted that a relationship record 809 can be thought of as "belonging" to two nodes—the start node and the end node of the relationship. To avoid storing two relationship records and to make the relationship record belong to both the start node and the end node, there are pointers (aka record IDs) for two doubly linked lists: one is the list of relationships visible from the start node; the other is the list of relationships visible from the end node. This provide rapid iteration through that list in either direction, and efficient insertion or deletion of relationships.

Choosing to follow a different relationship involves iterating through a linked list of relationships until a candidate matching the correct type or having some matching property value is found. The found relationship gives a new ID. The new ID is multiplied by record size as a new pointer and the traversal continues. With fixed-sized records and pointer-like record IDs, traversals are implemented simply by chasing pointers around a data structure, which can be performed at very high speed. To traverse a particular relationship from one node to another, the database performs several cheap ID computations (these computations are much cheaper than searching global indexes, as would be required if faking a graph in a non-graph native database). First, from a given node record, the first record in the relationship chain is located by computing its offset into the relationship store—that is, by multiplying its ID by the fixed relationship record size (e.g., 33 bytes). This gets to the right record in the relationship store. Then, from the relationship record, look in the second node field to find the ID of the second node. Multiply that ID by the node record size (e.g., nine bytes) to locate the correct node record in the store.

In addition to the node and relationship stores, which contain the graph structure, systems include the property store files. These store the user's key-value pairs. Properties may be attached to both nodes and relationships. The property stores, therefore, are referenced from both node and relationship records. Records in the property store are physically stored in a file. As with the node and relationship stores, property records are of a fixed size. Each property record consists of four property blocks and the ID of the next property in the property chain. Properties are held as a singly linked list on disk as compared to the doubly linked list used in relationship chains. Each property occupies between one and four property blocks—a property record can, therefore, hold four properties. A property record holds the property type and a pointer to the property index file, which is where the property name is stored. For each property's value, the record contains either a pointer into a dynamic store record or an inlined value. The dynamic stores allow for storing large property values. A graph database may optimize storage where it inlines some properties into the property store file directly. This happens when property data can be encoded to fit in one or more of a record's four property blocks. In practice this means that data like variant calls can be inlined in the property store file directly, rather than being pushed out to the dynamic stores. This results in reduced I/O operations and improved throughput, because only a single file access is required.

In addition to in-lining certain compatible property values, a graph database can also reference long values as property names (e.g., complete journal article titles and citations). In such cases, property names are indirectly referenced from the property store through the property index file. The property index allows all properties with the same name to share a single record, and thus for repetitive graphs achieves considerable space and I/O savings.

To improve the performance characteristics of mechanical/electronic mass storage devices, many graph databases use in-memory caching to provide probabilistic low latency access to the graph. Neo4j uses a two-tiered caching architecture to provide this functionality.

The lowest tier in the Neo4j caching stack is the file system cache 741. The file system cache 741 is a page-affined cache, meaning the cache divides each store into discrete regions, and then holds a fixed number of regions per store file. The actual amount of memory to be used to cache the pages for each store file can be fine-tuned, though in the absence of input from the user, Neo4j will use sensible default values based on the capacity of the underlying hardware. Pages are evicted from the cache based on a least-frequently-used (LFU) cache policy.

The file system cache 741 is particularly beneficial when related parts of the graph are modified at the same time such that they occupy the same page. This is a common pattern for writes, where whole sub-graphs (such as a patient's NGS results and associated carrier screening report) are written to disk in a single operation, rather than discrete nodes and relationships.

A graph database may be manipulated through a query language, which can be either imperative or declarative. One such language is the Cypher query language. Cypher is a declarative graph query language for Neo4j that allows for expressive and efficient querying and updating of the graph store. Cypher contains a variety of clauses, some of the most common of which include MATCH and WHERE. These functions are slightly different than in SQL. MATCH is used for describing the structure of the pattern searched for, primarily based on relationships, and WHERE is used to add additional constraints to patterns. Cypher additionally contains clauses for writing, updating, and deleting data. CREATE and DELETE are used to create and delete nodes and relationships. SET and REMOVE are used to set values to properties and add labels on nodes.

Systems and methods of the invention provide very rapid transactions, idiomatic queries, and an excellent ability to "scale up" with very large data sizes. The topic of scale has become more important as data volumes have grown. Graph databases don't suffer the same latency problems as traditional relational databases, where the more data that exists in tables—and in indexes—the longer the join operations. With a graph database, most queries follow a pattern whereby an index is used simply to find a starting node (or nodes). The remainder of the traversal then uses a combination of pointer chasing and pattern matching to search the data store. What this means is that, unlike relational databases, performance does not depend on the total size of the dataset, but only on the data being queried. This leads to performance times that are nearly constant (i.e., are related to the size of the result set), even as the size of the dataset grows. Throughput, speed, and scalability of graph databases make them suited to genetic analysis and reporting. Given the input/output-intensive nature of such sequencing, variant-calling, genotyping, and clinical reporting, a typical operation reads and writes a set of related data. In other words, the application performs multiple operations on a logical sub-graph within the overall dataset. With a graph database such multiple operations can be rolled up into larger, more cohesive operations. Further, with a graph-native store, executing each operation takes less computational effort than the equivalent relational operation. Graphs scale by doing less work for the same outcome.

Figure 9:
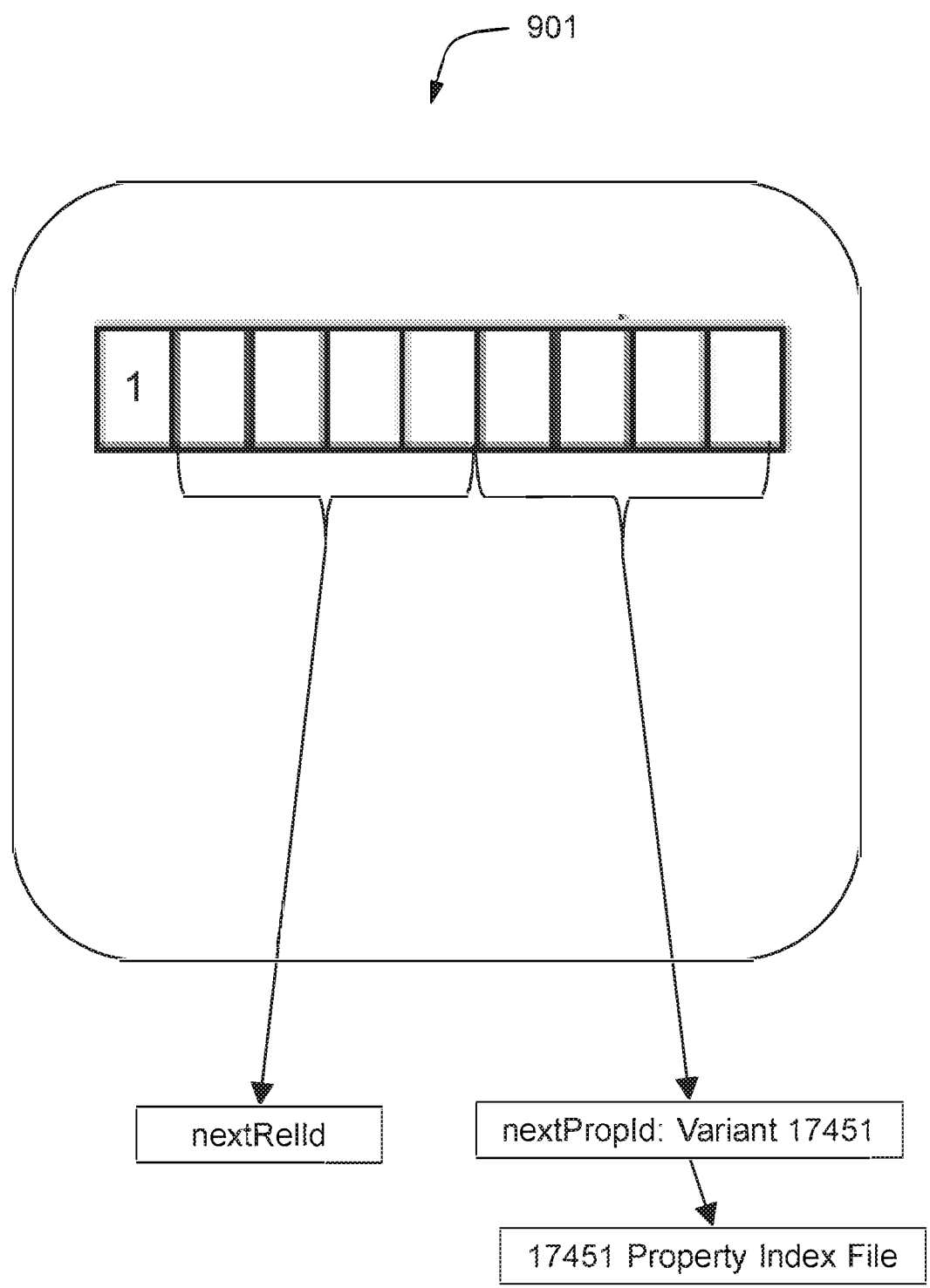
FIG. 9 illustrates the use of a variant node to store a description of a mutation.

FIG. 9 illustrates the use of a variant node 901 in a graph database to store a description of a mutation. The first byte of the variant node 901 record is set to show that node 901 is in use. The next four bytes of node 901 represent the ID of the first relationship connected to the node. Through the ID of that first relationship, node 901 thus includes a pointer to an adjacent node (adjacent by definition, since the relationship is identified by the four bytes in node 901). The last four bytes of node 901 represent the ID of the first property for the node.

To read the first property for node 901, one may follow the singly linked list structure to the appropriate property record in the property store. Property records in the property store are of a fixed size and each property record consists of four property blocks and the ID of the next property in the chain. The property record holds the property type (here, "variant") and a pointer to the property index file, which is where the property name is stored. For each property's value, the record either points to a dynamic store or an inline record. Here, the parser operating via the logic mapped in FIG. 4 produces a record of a mutation (by parsing that record from the VCF file) and can store that mutation in the property index file. Thus the property index file for a variant node preferably includes a description of a mutation.

A description of a mutation may be provided according to a systematic nomenclature. For example, a variant can be described by a systematic comparison to a specified reference which is assumed to be unchanging and identified by a unique label such as a name or accession number. For a given gene, coding region, or open reading frame, the A of the ATG start codon is denoted nucleotide+1 and the nucleotide 5' to +1 is −1 (there is no zero). A lowercase g, c, or m prefix, set off by a period, indicates genomic DNA, cDNA, or mitochondrial DNA, respectively.

A systematic name can be used to describe a number of variant types including, for example, substitutions, deletions, insertions, and variable copy numbers. A substitution name starts with a number followed by a "from to" markup. Thus, 199A>G shows that at position 199 of the reference sequence, A is replaced by a G. A deletion is shown by "del" after the number. Thus 223delT shows the deletion of T at nt 223 and 997-999del shows the deletion of three nucleotides (alternatively, this mutation can be denoted as 997-999delTTC). In short tandem repeats, the 3' nt is arbitrarily assigned; e.g. a TG deletion is designated 1997-1998delTG or 1997-1998del (where 1997 is the first T before C). Insertions are shown by ins after an interval. Thus 200-

201insT denotes that T was inserted between nts 200 and 201. Variable short repeats appear as 997(GT)N-N'. Here, 997 is the first nucleotide of the dinucleotide GT, which is repeated N to N' times in the population.

Variants in introns can use the intron number with a positive number indicating a distance from the G of the invariant donor GU or a negative number indicating a distance from an invariant G of the acceptor site AG. Thus, IVS3+1C>T shows a C to T substitution at nt+1 of intron 3. In any case, cDNA nucleotide numbering may be used to show the location of the mutation, for example, in an intron. Thus, c.1999+1C>T denotes the C to T substitution at nt+1 after nucleotide 1997 of the cDNA. Similarly, c.1997-2A>C shows the A to C substitution at nt −2 upstream of nucleotide 1997 of the cDNA. When the full length genomic sequence is known, the mutation can also be designated by the nt number of the reference sequence.

Relative to a reference, a patient's genome may vary by more than one mutation, or by a complex mutation that is describable by more than one character string or systematic name. The invention further provides systems and methods for describing more than one variant using a systematic name. For example, two mutations in the same allele can be listed within brackets as follows: [1997G>T; 2001A>C]. Systematic nomenclature is discussed in den Dunnen & Antonarakis, 2003, Mutation Nomenclature, Curr Prot Hum Genet 7.13.1-7.13.8 as well as in Antonarakis and the Nomenclature Working Group, 1998, Recommendations for a nomenclature system for human gene mutations, Human Mutation 11:1-3. By such means, a mutation can be described in the property index file of a variant node.

While described here with reference to FIG. 9 as a "variant node", it will be appreciated that node 901 can be instantiated or used as any type, with the type being stored in the property store.

Figure 10:
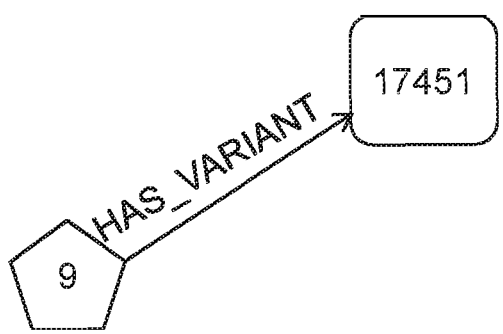
FIG. 10 shows an allele node showing that an allele includes a certain mutation.

FIG. 10 illustrates a simple example in which an allele node is used to show that an allele includes a certain mutation by representing the mutation using a variant node and representing a relationship between the allele node and the variant node with a "HAS_VARIANT" type relationship. This illustrates the simplicity of connecting alleles to variants using relationships. After the variant is created, literature references can be added to the variant.

Figure 11:
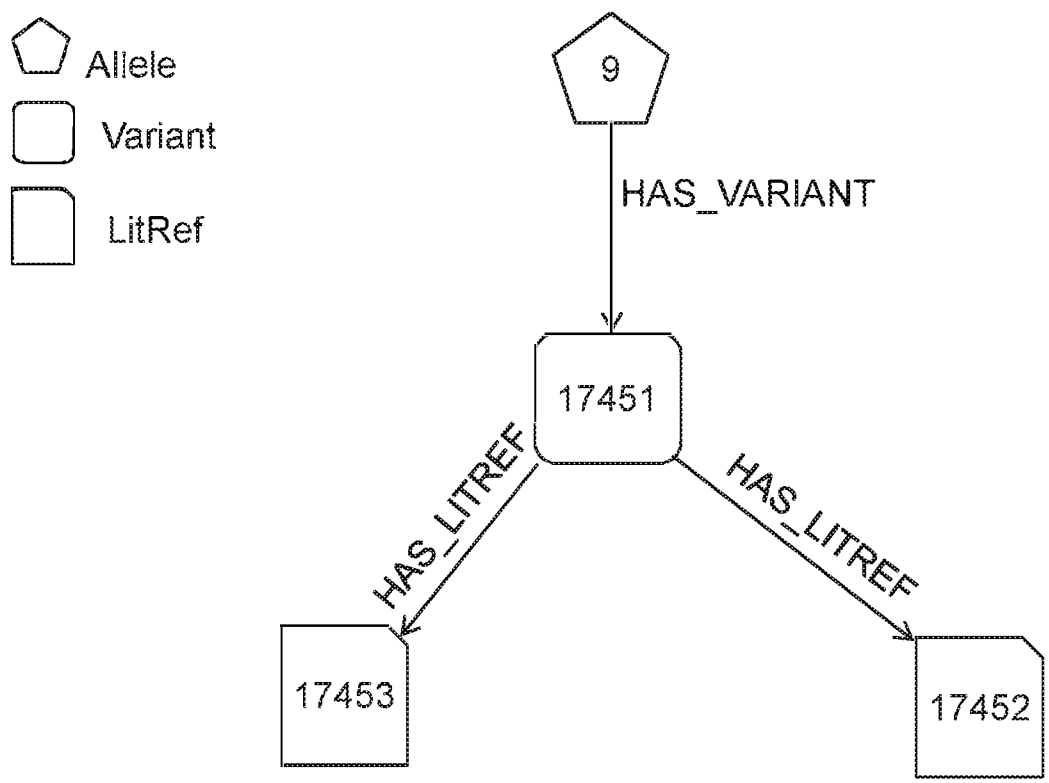
FIG. 11 shows variant node connected to two different literature reference nodes.

FIG. 11 shows elements of a graph database in which a variant has been connected to two nodes, each for a literature reference. From this setup emerges one of the powerful applications of a graph database in processing results from NGS sequencing data. If variant changes are made, those variant changes can be tracked within systems of the invention without requiring upsetting the structure of the existing database.

To illustrate the invention by an example, a patient sample could be sequenced via NGS technologies and the sequencing results could include, in a VCF file, a description of a mutation in that patient's mitochondrial genome. A variant node is used and a property of that node (e.g., in a property index file) is used to describe that mutation as m.593T>C. A relationship is created to shown that the mutation is described in a literature reference. The relationship is a pointer to a LitRef node and the LitRef node points to a property index file that with information about the literature reference. The property index file contains Zhang et al., 2011, Is mitochondrial tRNAphe variant m.593T>C a synergistically pathogenic mutation in Chinese LHON families with m.11778G>A?, PLoS ONE 6(10):e26511. Based on the synergistic pathogenesis alluded to by the literature reference, a geneticist or curator may deem it important to flag instances in which a patient has both m.593T>C and m.11778G>A in their genome. This example illustrates the real power of a graph database and index-free adjacency. A query can be initiated that starts at the LitRef node just described and traverses to the variant node. That query can traverse to the sample node for that patient and even to a node for the patient. That query can then—by its own terms—traverse from the patient or sample node examining for the presence of a second variant node representing m.11778G>A. The query can be programmed to, in the absence of said second variant node, classify the mutation as benign. The query can be programmed to, in the presence of said second variant node, classify the mutation as pathogenic. Intermediate labels or other categories can also be used. Since the query is traversing across a graph database, a comprehensive index-based look-up is not required as would be required in prior art RDMSs.

It is important to note that the "graph" of the described graph databases follows the counter-intuitive path of connecting things of un-related categories. Although it is not the primary structure or purpose described herein, one may imagine embodiments in which a graph has a horizontal structure connecting entities that are essentially similar in nature so that the database maps a natural phenomenon. For example, a graph database could represent protein interactions using the edges (aka pointers or relationships) to represent interactions between proteins and thus influxes of data would expand the graph "horizontally". However, the invention is unlike the protein interaction example in that the graph expands "vertically" outside of a set of natural phenomena. Since a sample can have a node, the graph can reach to laboratory management systems and receive from or provide information to, for example, sample chain of custody modules. With NGS results from that sample, the graph can leap vertically to a genetic plane and represent human mutations that are being discovered. For NGS carrier screening application, the graph can reach vertically into a different category to represent medical literature, and can go on to be used patient reports. The power of this novel vertical structure is shown by the illustration of use of the invention for reporting carrier screening results.

Figure 12:
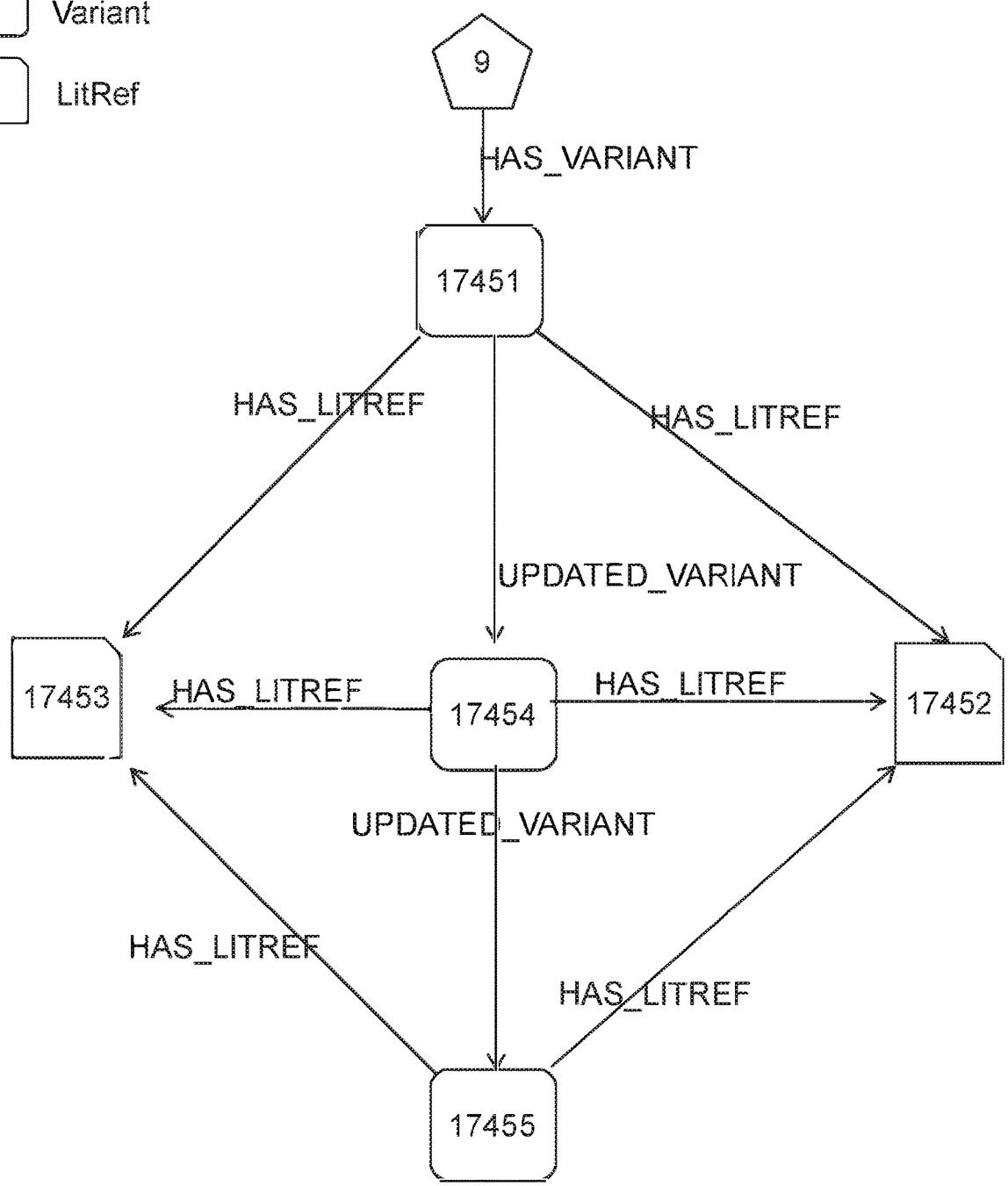
FIG. 12 illustrates updating information about a mutation.

FIG. 12 illustrates a graph database in which a variant has been connected to two nodes, each for a literature reference and in which updated information about the variant has been introduced in two changes. For example, node 17451 may represent a specific mutation such as a SNP (e.g., G at a certain position). Node 17454 could be created when A is observed at that position.

Systems and methods of the invention support a plurality of different use cases and applications. For example, if a graph database is used in support of NGS carrier screening, one capability that will emerge is support for evaluating and reporting allele frequency.

For example, where a practitioner wants to know, across all included research consenting data, what is the frequency of a certain allele, the graph database can easily be queried for that.

Figure 13:
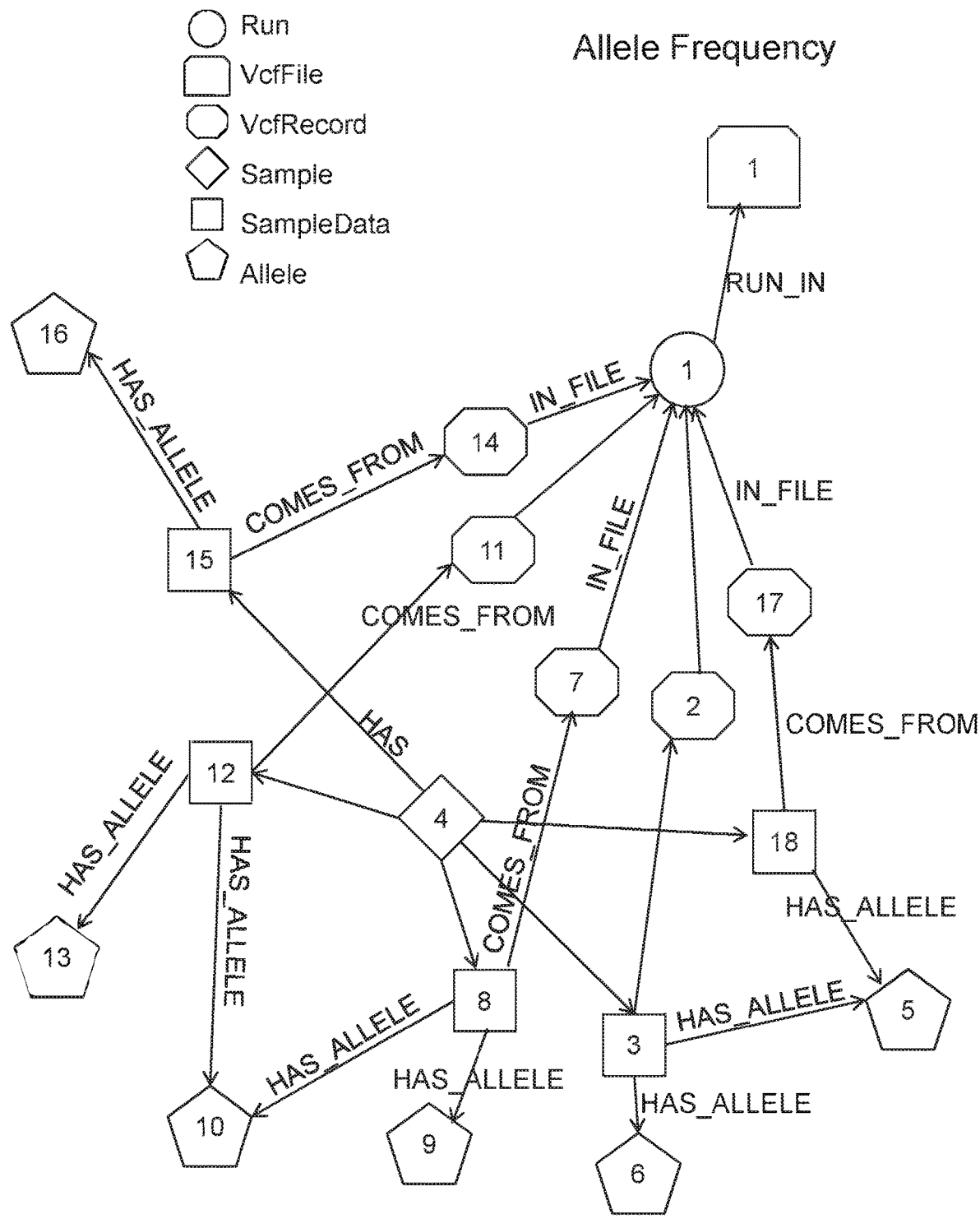
FIG. 13 presents an example database that may be queried for allele frequency.

FIG. 13 presents an example database that may be queried for allele frequency.

Using—for example, in Cypher—the following (pseudo) code produces the desired result.
MATCH (a:Allele)←(sd:S ampleData)→(s:Sample)→p:Patient) RETURN a,count(distinct p)

Another illustrative use case for application of a graph database is the curation of variants. As was illustrated by FIGS. 10-12. The curation of variants involves taking variants (i.e. genetic mutations) that have been picked up through a sequencing platform and then looking through the literature for references to evaluate how common the variant is and whether it is identified as pathogenic, benign, or somewhere in-between. This can be supported and modeled by tracking three things: connecting allele to a variant; variant and variant changes; and literature references per variant. To illustrate, a geneticist may observe review a patient's NGS sequencing results and observe the presence of a poly-T variant. The geneticist may connect this variant to an allele of the cystic fibrosis transmembrane conductance receptor (CFTR) gene located on the long arm of chromosome 7 (e.g., as shown in FIG. 10). The geneticist may further observe that this variant is described by a literature reference and connect the variant object to two different LitRef objects such as one for each of Rowntree and Harris, The phenotypic consequences of CFTR mutations, Ann Hum Gen 67:471-485 (2003) and Kreindler, Cystic fibrosis: exploiting its genetic basis in the hunt for new therapies, Pharmacol Ther 125(2):219-229 (2010) (e.g., according to the diagram of FIG. 11). Moreover the geneticist may observe that the mutation (the poly-T) is a novel poly-T variant in the acceptor splice site of intron 8 of CFTR in cis with R117H (i.e., c.350G>A based on GenBank cDNA reference sequence NM_000492.3). In this instance, the geneticist may want to update the graph for this patient by connecting the poly-T mutation to a variant object for c.350G>A (e.g., as seen in FIG. 12). To further illustrate, the chain of updated variants may reveal that the patient has an allele with the T5 poly-T variant, which evidence suggests plays a role in in pathogenic alternate splicing or exon skipping. Moreover, the geneticist may further consider the data and determine that, in-fact, the patient's allele includes a T6 form of the poly-T variant and may update the variant nodes to so reflect. Here, with the addition of a T6 node, other content need not be modified. The geneticist may add a LitRef node for Huang, et al., Comparative analysis of common CFTR polymorphisms poly-T, TG-repeats and M470V in a healthy Chinese population, World J Gastroenterol 14(12):1925-30 (2008). Thus if the NGS screening gave results indicating a R117H with T6 variant, methods and systems of the invention can be used to relate this clinical results data to the existing infrastructure of medical information on one level and back to the patient via the sample (through the VCF files and instrument run) on another level. Since a graph database preferably with index-free adjacency is used for each node, those connections can be traversed to provide a report to the patient's attending physician, where the report shows the patient to be R117H T6 and gives the relevant literature with information about treatment and outcomes. Since a graph database is used, the traversals are very fast and traversal times do not increase with increasing volumes of database contents as queries times must so increase in the context of prior art relational databases.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

Figure 14:
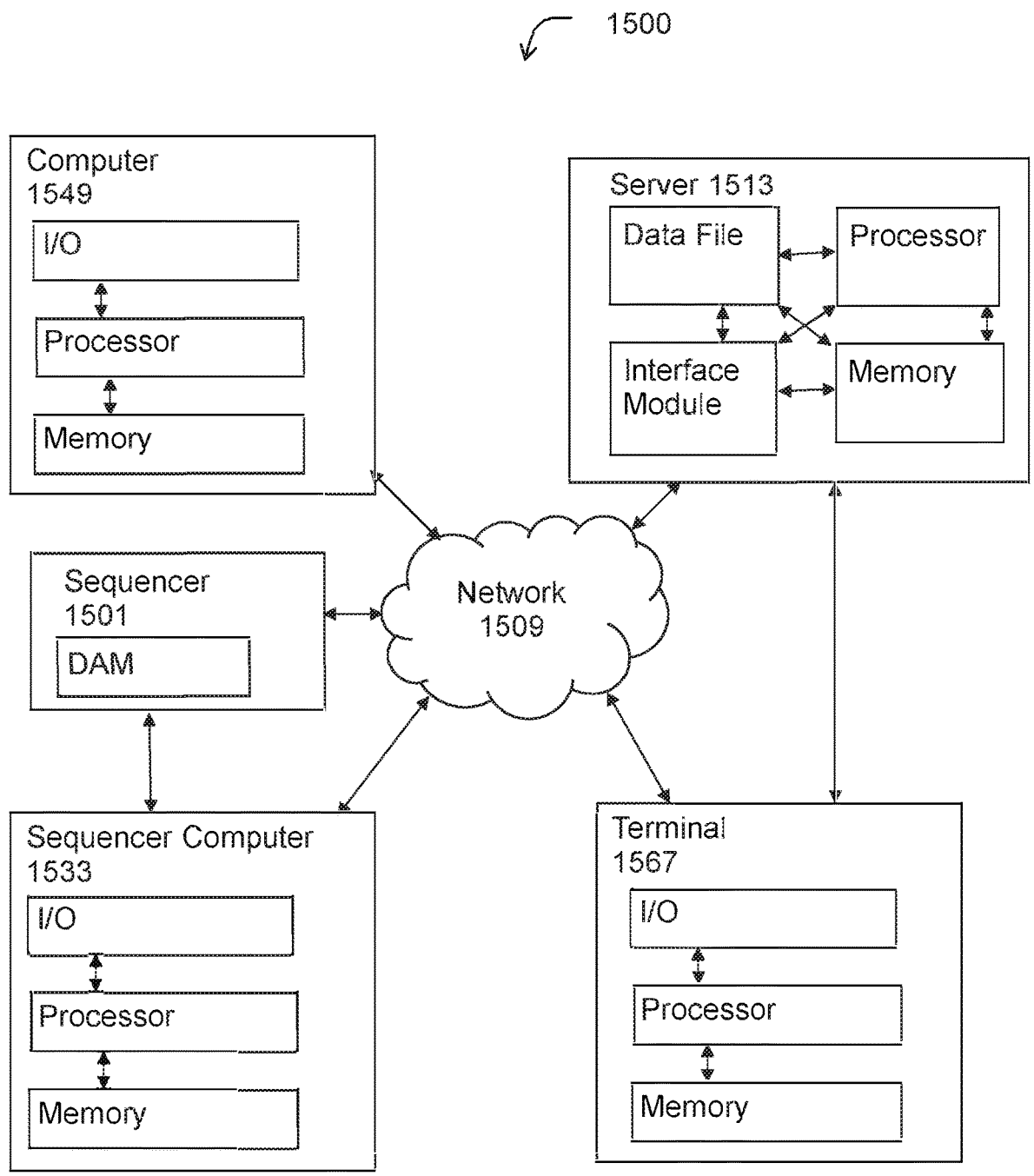
FIG. 14 diagrams a system for performing methods of the invention.

FIG. 14 diagrams a system 1500 suitable for performing methods of the invention. As shown in FIG. 14, system 1500 may include one or more of a server computer 1513, a terminal 1567, a sequencer 1501, a sequencer computer 1533, a computer 1549, or any combination thereof. Each such computer device may communicate via network 1509.

Sequencer 1501 may optionally include or be operably coupled to its own, e.g., dedicated, sequencer computer 1533 (including any input/output mechanisms (I/O), processor, and memory). Additionally or alternatively, sequencer 1501 may be operably coupled to a server 1513 or computer 1549 (e.g., laptop, desktop, or tablet) via network 1509. Computer 1549 includes one or more processor, memory, and I/O. Where methods of the invention employ a client/server architecture, any steps of methods of the invention may be performed using server 1513, which includes one or more of processor, memory, and I/O, capable of obtaining data, instructions, etc., or providing results via an interface module or providing results as a file. Server 1513 may be engaged over network 1509 through computer 1549 or terminal 1567, or server 1513 may be directly connected to terminal 1567. Terminal 1567 is preferably a computer device. A computer according to the invention preferably includes one or more processor coupled to an I/O mechanism and memory.

A processor may be provided by one or more processors including, for example, one or more of a single core or multi-core processor (e.g., AMD Phenom II X2, Intel Core Duo, AMD Phenom II X4, Intel Core i5, Intel Core i& Extreme Edition 980X, or Intel Xeon E7-2820).

An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system 1500, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

Components of system 1500 may be under the control of a carrier screening service provider and may be operated to obtain data representing a mutation in a genome of an individual, use a variant node in a graph database to store a description of the mutation (while storing, in the variant node, a pointer to an adjacent node that provides information about a clinical significance of the variant), and query the graph database to provide a report of the clinical significance of the mutation in the genome of the individual. Functionality of server computer 1513 may be provided by an outside vendor such as Amazon Web Services or Amazon's EC2. In fact, the carrier screening entity who is analyzing the mutations from the sample may not and need not have actual knowledge of the physical location and type of computers that provide server computer(s) 1513. It is enough that the entity have access to and the ability to control at least a portion of each of one or more of server computer 1513. In some embodiments, a sequencing instrument 1501 is employed (e.g., an Illumina HiSeq 2000), which itself includes a sequencer computer 1533). The sample from the patient may be received from an outside source (e.g., from a phlebotomy facility down the hall or may be sent by courier (e.g., in an Eppendorf tube). Generally, the service provider will have access to and use a computer 1549 for coordinating methods of the invention. It is important to note that any given computer is optional but typically at least one of the depicted computer (sequencer computer 1533, local computer 1549, or server computer 1513) will be used to perform steps of the methods of the invention. In some embodiments, sequencer 1501 is operated by an outside service provider in support of or on order of the carrier screening entity. Thus generally the carrier screening professional has access to or control over components of the system.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:
1. A system for describing genetic information, the system comprising:
 a memory configured to store:
  a graph database comprising at least:
   an allele node storing a first relationship record identifier (ID) and an allele pointer to allele information about an allele, the allele information included in genomic information of a sample obtained from an individual,
   a mutation node storing a second relationship record ID and a first mutation pointer to mutation information about a mutation in the allele, and
   a clinical significance node storing the second relationship record ID and a first mutation pointer to clinical significance information about the mutation; and
  wherein each of the allele node, mutation node, and clinical significance node has a first fixed size; and
  a relationship data structure comprising at least:
   a first relationship record located by the first relationship record ID comprising an allele node ID, a mutation node ID, a first relationship type between the allele node and the mutation node, and a first pointer to a second relationship record, and
   the second relationship record located by the second relationship record ID comprising the mutation node ID, a clinical significance node ID, a second relationship type between the mutation node and the clinical significance node, and a second pointer to the first relationship record; and
  wherein each of the first relationship record and the second relationship record has a second fixed size; and
 a processor coupled to the memory, the processor configured to:
  receive updated information about the mutation and updated information about the clinical significance of the mutation;
  generate an updated mutation node having the first fixed size in the graph database, the updated mutation node comprising a third relationship record ID and a second mutation pointer to the updated information about the mutation;
  generate an updated clinical significance information node having the first fixed size in the graph database, the updated clinical significance information node comprising a fourth relationship record ID and a second clinical significance pointer to the updated information about the clinical significance of the mutation;
  generate a third relationship record having the second fixed size in the relationship data structure, the third relationship record comprising an updated mutation node ID, the mutation node ID, a third relationship type of the updated mutation node and the mutation node, and a third pointer to the mutation node, wherein a location of the third relationship record in the relationship data structure is determined based on the third relationship record ID and the second fixed size;
  generate a fourth relationship record having the second fixed size in the relationship data structure, the fourth relationship record comprising an updated clinical significance node ID, the updated mutation node ID, a fourth relationship type of the updated clinical significance and updated mutation node, and a fourth pointer to the updated mutation node, wherein a location of the fourth relationship record in the relationship data structure is determined based on the fourth relationship record ID and the second fixed size, wherein the first relationship record through the fourth relationship record make up a relationship chain in the relationship data structure; and
  generate a report of a clinical significance of the mutation in the allele based on the first through fourth relationship records by traversing the relationship chain in the relationship data structure using the first through fourth relationship record IDs.

2. The system of claim 1, wherein traversing the relationship chain comprises:
selecting one of the allele node, the mutation node, the clinical significance node, the updated clinical significance node, and the updated mutation node as a starting node;
determining a location of the starting node in the graph database based on an identifier of the starting node and the first fixed size a size of ; and
determining locations of other nodes in the graph database based on the relationship chain including the first through fourth relationship records.

3. The system of claim 1, wherein, to generate the report, the processor is further configured to:
receive a query to retrieve information regarding the mutation, wherein the query indicates a starting node to start the query, and wherein the starting node is one of the allele node, the mutation node, the clinical significance node, the updated mutation node, or the updated clinical significance node;
determine relevant nodes from at least one of the allele node, the mutation node, the clinical significance node, the updated mutation node, or the updated clinical significance node for generating the report of the clinical significance of the mutation; and
starting at the starting node, traverse the relevant nodes to generate the report of the clinical significance of the mutation based on the relationship chain in the relationship data structure.

4. The system of claim 1, wherein a plurality of edges connect the allele node, the mutation node, the clinical significance node, the updated clinical significance node, and the updated mutation node, based on the first through fourth relationship record IDs in the relationship chain.

5. The system of claim 1, wherein the information about the mutation includes a description of the mutation as a variant of a reference human genome.

6. The system of claim 1, wherein the data including the updated information includes sequence read data.

7. The system of claim 1, wherein the data including the updated information is received as a ASTA file, FASTQ file, Sequence Alignment Map (SAM) file, Binary Alignment Map (BAM) file, or VCF file.

8. The system of claim 1, wherein the mutation information is obtained by sequencing the sample.

9. A method for describing genetic information, the method comprising:
receiving, by one or more computing devices, updated information about a mutation of an allele to be stored in a data storage device including a graph database and a relationship data structure, wherein the graph database comprises a first plurality of nodes storing a first relationship record identifier (ID) and an allele pointer to allele information about the allele, a second relationship record ID and a first mutation pointer to mutation information about the mutation of the allele, and the second relationship record ID and a first clinical significance pointer to clinical significance information of the mutation, wherein each node in the first plurality of nodes has a first fixed size;
generating, by the one or more computing devices, a first new node having the first fixed size in the graph database comprising a third relationship record ID and a second mutation pointer to updated information about the mutation, in response to receiving the updated information about the mutation;
determining, by the one or more computing devices, updated clinical significance information of the mutation based on the updated information about the mutation;
generating, by the one or more computing devices, a second new node having the first fixed size in the graph database comprising a fourth relationship record ID and a second clinical significance pointer to the updated clinical significance information of the mutation, wherein the first new node and the second new node are added to the plurality of nodes of the graph database;
forming, by the one or more computing devices, a relationship chain in the relationship data structure, the relationship chain comprising a second plurality of nodes storing an allele node ID, a mutation node ID, a clinical significance node ID, a first new node ID, and a second new node ID, wherein each node in the second plurality of nodes has a second fixed size; and
generating, by the one or more computing devices, a report of a clinical significance of the mutation in the allele by traversing the relationship chain in the relationship data structure using the first through fourth relationship record IDs.

10. The method of claim 9, wherein traversing the relationship chain comprises:
selecting, by the one or more computing devices, one of the first plurality of nodes as a starting node;
determining, by the one or more computing devices, a location of the starting node in the graph database based on an identifier of the starting node and the first fixed size; and
determining, by the one or more computing devices, locations of other nodes in the graph database based on the relationship chain.

11. The method of claim 9, wherein generating the report comprises:
receiving, by the one or more computing devices, a query to retrieve information regarding the mutation, wherein the query indicates a starting node to start the query;
determining, by the one or more computing devices, relevant nodes from the at least one of the first plurality of nodes for generating the report of the clinical significance of the mutation; and
starting at the starting node, traversing, by the one or more computing devices, the relevant nodes to generate the report of the clinical significance of the mutation based on the relationship chain in the relationship data structure.

12. The method of claim 9, wherein a plurality of edges connect the first plurality of nodes based on the first through fourth relationship record IDs in the relationship chain.

13. The method of claim 9, wherein the information about the mutation includes a description of the mutation as a variant of a reference human genome.

14. The method of claim 9, wherein the updated information about the mutation includes sequence read data.

15. A non-transitory computer-readable medium having instructions stored thereon, execution of which, by one or more processors of a device, cause the one or more processors to perform operations comprising:
receiving updated information about a mutation of an allele to be stored in a data storage device including a graph database and a relationship data structure, wherein the graph database comprises a first plurality of nodes storing a first relationship record identifier (ID) and an allele pointer to allele information about the allele, a second relationship record ID and a first mutation pointer to mutation information about the mutation of the allele, and the second relationship record ID and a first clinical significance pointer to clinical significance information of the mutation, wherein each node in the first plurality of nodes has a first fixed size;

generating a first new node having the first fixed size in the graph database comprising a third relationship record ID and a second mutation pointer to updated information about the mutation, in response to receiving the updated information about the mutation;

identifying updated clinical significance information of the mutation based on the updated information about the mutation;

generating a second new node having the first fixed size in the graph database comprising a fourth relationship record ID and a second clinical significance pointer to the updated clinical significance information of the mutation, wherein the first new node and the second new node are added to the first plurality of nodes of the graph database;

forming a relationship chain in the relationship data structure, wherein the relationship chain comprises a second plurality of nodes storing an allele node ID, a mutation node ID, a clinical significance node ID, a first new node ID, and a second new node ID, wherein each node in the second plurality of nodes has a second fixed size; and generating a report of a clinical significance of the mutation in the allele by traversing the relationship chain in the relationship data structure using the first through fourth relationship record IDs.

16. The non-transitory computer-readable medium of claim 15, wherein the operations for traversing the relationship chain further comprise:

selecting one of the first plurality of nodes as a starting node;

determining a location of the starting node in the graph database based on an identifier of the starting node and the first fixed size ; and determining locations of other nodes in the graph database based on the relationship chain.

17. The non-transitory computer-readable medium of claim 15, wherein the operations for generating the report further comprise:

receiving a query to retrieve information regarding the mutation, wherein the query indicates a starting node to start the query;

determining relevant nodes from at least one of the first plurality of nodes for generating the report of the clinical significance of the mutation; and starting at the starting node, traversing the relevant nodes to generate the report of the clinical significance of the mutation based on the relationship chain in the relationship data structure.

* * * * *

UNITED STATES PATENT AND TRADEMARK OFFICE
CERTIFICATE OF CORRECTION

| | |
|---|---|
| PATENT NO. | : 12,386,895 B2 |
| APPLICATION NO. | : 17/000054 |
| DATED | : August 12, 2025 |
| INVENTOR(S) | : Alexander Frieden et al. |

Page 1 of 1

It is certified that error appears in the above-identified patent and that said Letters Patent is hereby corrected as shown below:

In the Claims

In Claim 2, at Column 29, Line 12:
"the first fixed size a size of ;"
Should read:
-- the first fixed size; --

Signed and Sealed this
Thirtieth Day of December, 2025

John A. Squires
*Director of the United States Patent and Trademark Office*